(12) United States Patent
Ono et al.

(10) Patent No.: US 10,830,737 B2
(45) Date of Patent: Nov. 10, 2020

(54) DETECTING DEVICE FOR DETECTING PHOTOACOUSTIC ELASTIC WAVES

(71) Applicant: TOHOKU UNIVERSITY, Sendai (JP)

(72) Inventors: Takahito Ono, Sendai (JP); Yoshinobu Ono, Tokyo (JP)

(73) Assignees: TOHOKU UNIVERSITY, Sendai (JP); NIHON KOHDEN CORPORATION, Tokyo (JP)

( * ) Notice: Subject to any disclaimer, the term of this patent is extended or adjusted under 35 U.S.C. 154(b) by 237 days.

(21) Appl. No.: 15/900,193

(22) Filed: Feb. 20, 2018

(65) Prior Publication Data
US 2018/0188212 A1 Jul. 5, 2018

Related U.S. Application Data

(63) Continuation of application No. PCT/JP2016/057271, filed on Mar. 9, 2016.

(30) Foreign Application Priority Data

Aug. 21, 2015 (JP) ................. 2015-163541

(51) Int. Cl.
*G01N 29/24* (2006.01)
*H04R 19/04* (2006.01)
(Continued)

(52) U.S. Cl.
CPC ......... *G01N 29/2406* (2013.01); *A61B 5/145* (2013.01); *G01N 29/022* (2013.01);
(Continued)

(58) Field of Classification Search
CPC ............... G01N 29/022; G01N 29/036; G01N 29/2406; G01N 29/2418; G01N 2291/0427; H04R 1/2838; H04R 19/04; H04R 19/005
See application file for complete search history.

(56) References Cited

U.S. PATENT DOCUMENTS 4,507,705 A * 3/1985 Hoshino ................. G01H 1/06
257/E27.006
4,571,661 A 2/1986 Hoshino
(Continued)

FOREIGN PATENT DOCUMENTS

EP 1 012 547 A1 6/2000
EP 2 579 616 A1 4/2013
(Continued)

OTHER PUBLICATIONS

International Search Report issued for corresponding International Patent Application No. PCT/JP2016/057271, dated Apr. 5, 2016.
(Continued)

*Primary Examiner* — Natalie Huls
(74) *Attorney, Agent, or Firm* — Myers Wolin, LLC.

(57) ABSTRACT

A detecting device 100 detects an elastic wave propagating through the air. The detecting device 100 includes: a first electrode 12 that is a plate having a cantilever structure with a fixed end FX and a free end FR and that vibrates by being bent by the elastic wave; and a second electrode 32 that is a plate, that is opposed to the first electrode, and that has a predetermined distance from the first electrode. The detecting device 100 detects the elastic wave on the basis of a change in capacitance between the first electrode and the second electrode 32. An end of the second electrode 32 in a direction from the fixed end FX to the free end FR is closer to the fixed end than the free end.

16 Claims, 18 Drawing Sheets

(51) Int. Cl.
  *G01N 29/036* (2006.01)
  *G01N 29/02* (2006.01)
  *H04R 19/00* (2006.01)
  *H04R 23/00* (2006.01)
  *H04R 1/28* (2006.01)
  *A61B 5/145* (2006.01)
  *G10H 3/00* (2006.01)
  *A61B 8/13* (2006.01)
  *A61B 8/00* (2006.01)
  *A61B 5/00* (2006.01)

(52) U.S. Cl.
  CPC ....... *G01N 29/036* (2013.01); *G01N 29/2418* (2013.01); *G10H 3/00* (2013.01); *H04R 19/04* (2013.01); *A61B 5/0095* (2013.01); *A61B 5/14532* (2013.01); *A61B 8/13* (2013.01); *A61B 8/4483* (2013.01); *A61B 2562/0214* (2013.01); *G01N 2291/0427* (2013.01); *H04R 1/2838* (2013.01); *H04R 19/005* (2013.01); *H04R 23/008* (2013.01)

(56) References Cited

U.S. PATENT DOCUMENTS

| | | | | |
|---|---|---|---|---|
| 4,672,849 | A * | 6/1987 | Hoshino | G01H 11/06 257/E27.006 |
| 4,890,480 | A * | 1/1990 | Young | G01N 9/002 73/32 A |
| 5,659,195 | A * | 8/1997 | Kaiser | G01P 15/0802 257/369 |
| 5,870,482 | A | 2/1999 | Loeppert et al. | |
| 5,925,822 | A * | 7/1999 | Naughton | G01H 11/06 367/103 |
| 7,696,587 | B2 * | 4/2010 | Watanabe | B81B 3/0086 257/414 |
| 2002/0194919 | A1 * | 12/2002 | Lee | G01L 9/0042 73/718 |
| 2003/0045019 | A1 * | 3/2003 | Kubena | B81C 1/00206 438/49 |
| 2006/0280319 | A1 * | 12/2006 | Wang | B81B 3/0072 381/172 |
| 2007/0154035 | A1 | 7/2007 | Fukui | |
| 2008/0290756 | A1 | 11/2008 | Huang | |
| 2009/0309173 | A1 * | 12/2009 | Nakatani | B81B 3/007 257/415 |
| 2010/0175477 | A1 * | 7/2010 | Kasai | H04R 19/005 73/649 |
| 2010/0254560 | A1 * | 10/2010 | Mehregany | H04R 19/005 381/361 |
| 2010/0259396 | A1 | 10/2010 | Watabe et al. | |
| 2011/0154905 | A1 * | 6/2011 | Hsu | G01L 9/0073 73/724 |
| 2013/0069179 | A1 | 3/2013 | Ishimoto et al. | |
| 2013/0089224 | A1 | 4/2013 | Dehe et al. | |
| 2015/0264464 | A1 * | 9/2015 | Okugawa | H04R 19/005 381/174 |
| 2016/0219378 | A1 * | 7/2016 | Hall | H04R 23/02 |
| 2018/0234783 | A1 * | 8/2018 | Clerici | H04R 3/002 |

FOREIGN PATENT DOCUMENTS

| | | |
|---|---|---|
| EP | 2 582 156 A2 | 4/2013 |
| JP | 2001-518246 A | 10/2001 |
| JP | 2008-42869 A | 2/2008 |
| JP | 2009-508367 A | 2/2009 |
| JP | 2010-73886 A | 4/2010 |
| WO | 98/37388 A1 | 8/1998 |
| WO | 2009/054359 A1 | 4/2009 |

OTHER PUBLICATIONS

Katsuhiko Maruo, "Study of noninvasive blood glucose measurement by using near-infrared spectroscopy" Graduate School of The University of Electro-Communications, p. 22, Jun. 2007, with English translation.

International Preliminary Report on Patentability of corresponding International Application No. PCT/JP2016/057271, dated Feb. 27, 2018. English translation attached.

Written Opinion of the International Searching Authority for corresponding International Application No. PCT/JP2016/057271, dated Apr. 5, 2016.

Extended European search report with supplementary European search report and the European search opinion issued by the European Patent Office for corresponding European Patent Application No. 16838829.6, dated Mar. 7, 2019.

* cited by examiner

FIG. 4
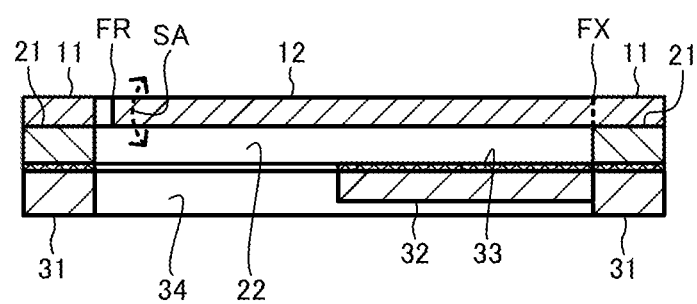
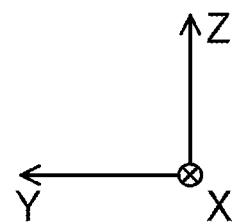

FIG. 10
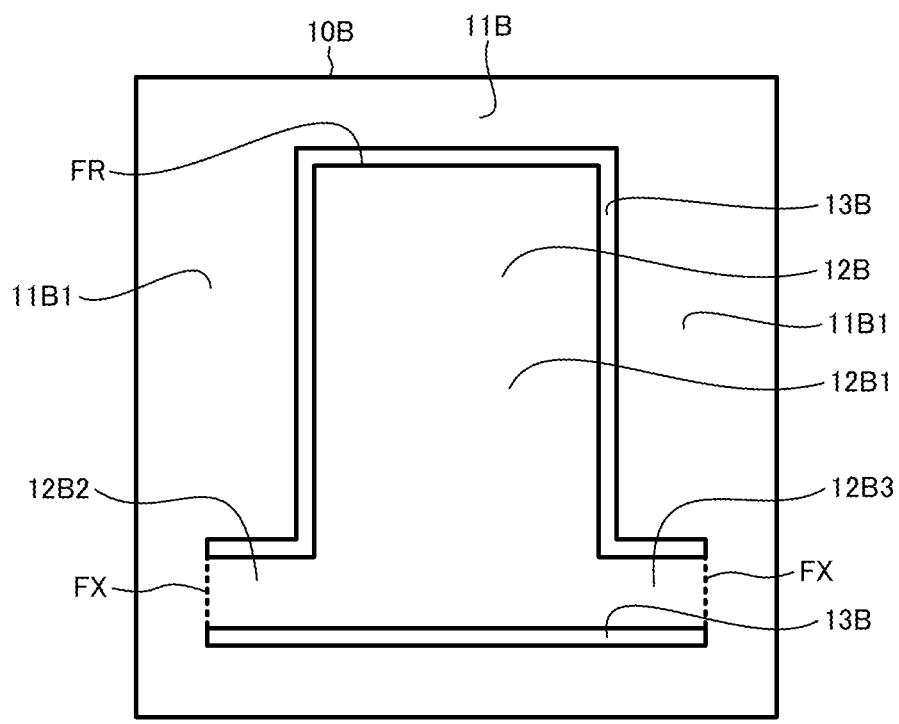
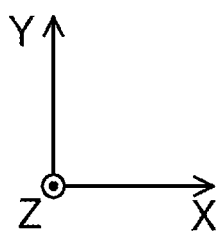

DETECTING DEVICE FOR DETECTING PHOTOACOUSTIC ELASTIC WAVES

CROSS-REFERENCE TO RELATED APPLICATIONS

This application is a continuation application of International Application PCT/JP2016/057271 filed on Mar. 9, 2016, which claims priority to Japanese Patent Application No. 2015-163541, filed on Aug. 21, 2015. The contents of these applications are incorporated herein by reference in their entirety.

The present invention relates to a detector and a detecting device.

BACKGROUND

One of the known detecting devices detects an elastic wave propagating through air. JP-T-2001-518246 discloses an example of a detecting device includes a first plate-shape electrode and a second plate-shape electrode being opposed to each other at a predetermined distance. The first electrode has a cantilever structure in which the opposite ends along a predetermined direction are a fixed end and a free end. The first electrode vibrates by being bent by the elastic wave. The detecting device detects the elastic wave on the basis of a change in capacitance between the first electrode and the second electrode.

SUMMARY

The free end of the first electrode undergoes a maximum displacement in the first electrode by the vibration among the positions of the first electrode. The distance from the fixed end to the end of the second electrode in the direction of from the fixed end to the free end is longer than the distance from the fixed end to the free end of the first electrode. This means that the second electrode extends to the position opposed to the free end of the first electrode in the above detection device. With this configuration, the air between the first and the second electrodes tends to attenuate the vibration of the first electrode in a larger extent. Consequently, there is possibility of not precisely detecting the elastic wave.

One of the objects of the present invention is to provide a detecting device that can precisely detect an elastic wave.

According to an aspect of the present invention, there is provided a detector that detects an elastic wave propagating through air. The detector includes a first electrode that is a plate having a cantilever structure with a fixed end and a free end and that vibrates by being bent by the elastic wave; and a second electrode that is a plate, that is opposed to the first electrode, and that has a predetermined distance from the first electrode. In addition, the detector detects the elastic wave on the basis of a change in capacitance between the first electrode and the second electrode. Furthermore, an end of the second electrode in a direction from the fixed end to the free end is closer to the fixed end than the free end.

According to another aspect, a detecting device that detects an elastic wave propagating through air, the detecting device includes: a detector that includes a first electrode that is a plate having a cantilever structure with a fixed end and a free end and that vibrates by being bent by the elastic wave; and a second electrode that is a plate, that is opposed to the first electrode, and that has a predetermined distance from the first electrode, the detector detecting the elastic wave on the basis of a change in capacitance between the first electrode and the second electrode, an end of the second electrode in a direction from the fixed end to the free end being closer to the fixed end than the free end; and a body that has an inner space being in contact with the detector and an opening being communicated with the inner space.

According to an additional aspect, a detecting device that detects an elastic wave propagating through air, the detecting device includes: a plurality of detectors each including a first electrode that is a plate having a cantilever structure with a fixed end and a free end and that vibrates by being bent by the elastic wave; and a second electrode that is a plate, that is opposed to the first electrode, and that has a predetermined distance from the first electrode, the detector detecting the elastic wave on the basis of a change in capacitance between the first electrode and the second electrode, an end of the second electrode in a direction from the fixed end to the free end being closer to the fixed end than the free end; a light source that generates light; and a processor that estimates a position of a wave source of the elastic wave on the basis of a time period from a time point at which the light is generated to a time point at which each of the plurality of detectors detects the elastic wave.

An elastic wave can be precisely detected.

BRIEF DESCRIPTION OF DRAWINGS

FIG. 4 is a sectional view of a detector along a line A-A of FIG. 3;

FIG. 10 is a front view of a detector according to a second modification to the first embodiment;

DESCRIPTION OF EMBODIMENT(S)

Hereinafter, description will now be made in relation to a detecting device according to various embodiments by referring to FIGS. 1-18.

First Embodiment

Figure 1:
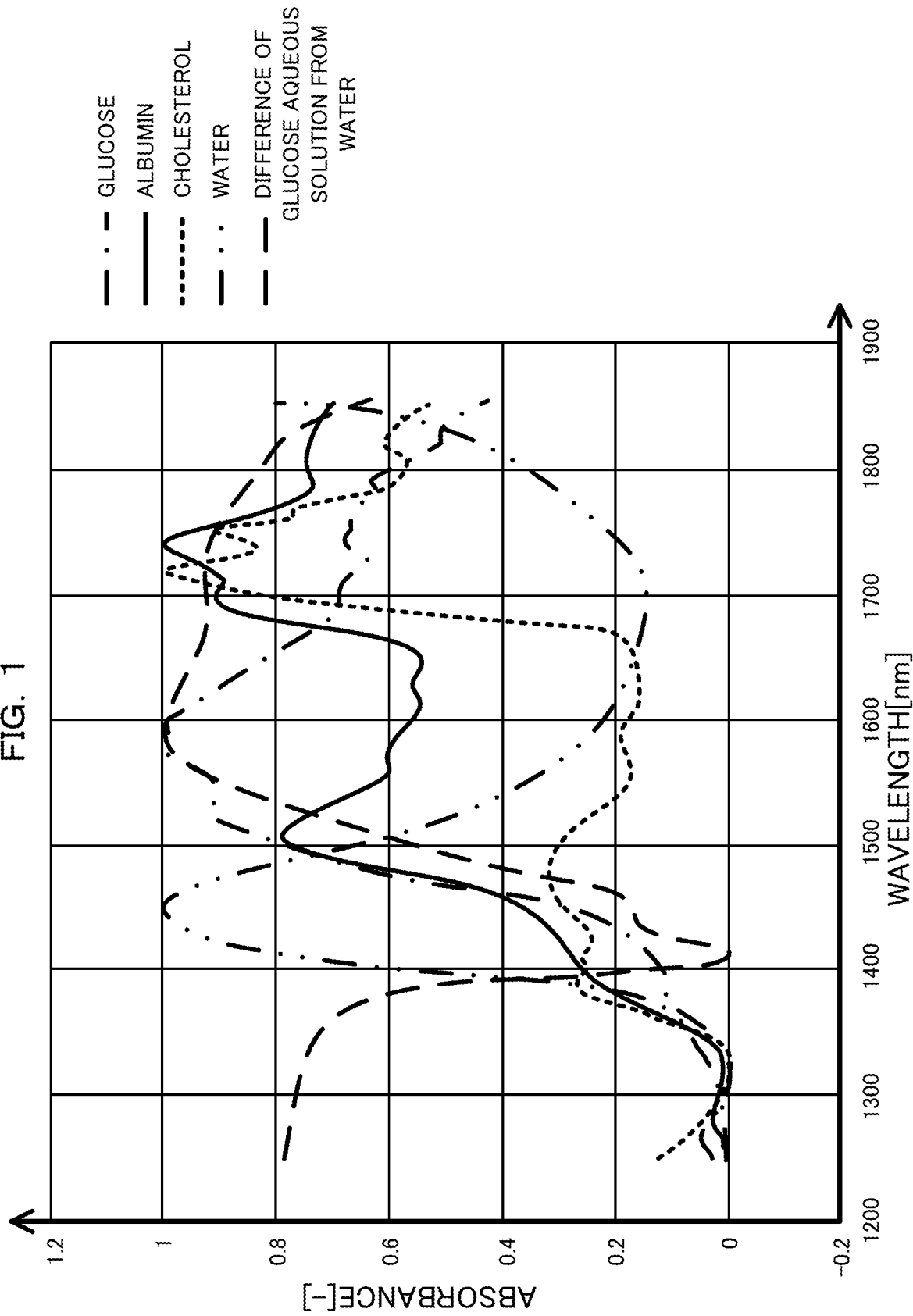
FIG. 1 is a graph depicting an example of a change of the absorbance of a target being irradiated with light in terms of the wavelength of the light.

It is known that irradiation of a target with light produces a photoacoustic effect that the target generates an elastic wave of a sound wave or ultrasound wave in response to the irradiation of light. FIG. 1 denotes a change in absorbance of a target, when being irradiated with light, in terms of the wavelength of the light. The absorbance here may also be referred to as an optical density. FIG. 1 cites FIG. 2.1 of Reference 1.

Reference 1: Katsuhiko MARUO, "Study of noninvasive blood glucose measurement by using near-infrared spectroscopy", theses for application for doctorate (Engineering) of Graduate School of Electro-Communications of Graduate School of The University of Electro-Communications, Graduate School of The University of Electro-Communications, P 22, June, 2007

The target is glucose powder, albumin powder, cholesterol powder, water, glucose aqueous solution of 10 g/dL. In FIG. 1, the absorbance of glucose aqueous solution is replaced by a difference of glucose aqueous solution from water obtained by subtracting the absorbance of water from the absorbance of glucose aqueous solution.

As depicted in FIG. 1, the change in absorbance of a target when being irradiated with light in terms of the wavelength of the light varies with target. The intensity of an elastic wave generated in response to the light that the target is irradiated with has a strong correlation with the absorbance. Accordingly, irradiation of a living body with light having a particular wavelength corresponding to a target in the living body makes it possible to precisely detect the target. Considering the above, the detecting device of the first embodiment detects a target by using the photoacoustic effect.

(Configuration)

Figure 2:
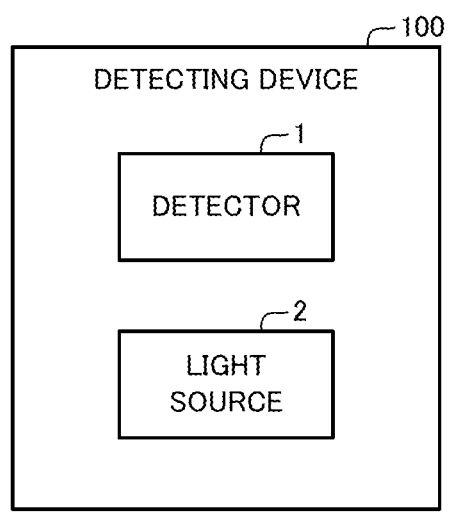
FIG. 2 is a block diagram illustrating an example of the configuration of a detecting device according to a first embodiment.

As illustrated in FIG. 2, a detecting device 100 of the first embodiment detects a target by using the photoacoustic effect. A target in this example is contained in the living body, and is exemplified by glucose, albumin, cholesterol, water, or tumor. For example, the detecting device 100 may detect swelling of the living body by detecting water served as the target.

The detecting device 100 includes a detector 1 and a light source 2.

The light source 2 generates laser light having a particular wavelength. In this example, the light source 2 performs a pulse-oscillation. Specifically, each time a predetermined oscillation cycle elapses, the light source 2 generates laser light (in other words, pulse laser light) having a predetermined intensity for a predetermined oscillation period. The oscillation cycle of this example is set to correspond to the resonance frequency $f_0$ of a first electrode 12 that is to be detailed below.

For example, the wavelength is in the range of 500 nm to 3000 nm; the oscillation cycle is in the range of 0.1 ms to 1 s; and the oscillation period is in the range of 0.01 ns to 0.1 ms. In this example, the wavelength is 905 nm; the oscillation cycle is 5 ms, and the oscillation period is 0.5 ns.

Figure 3:
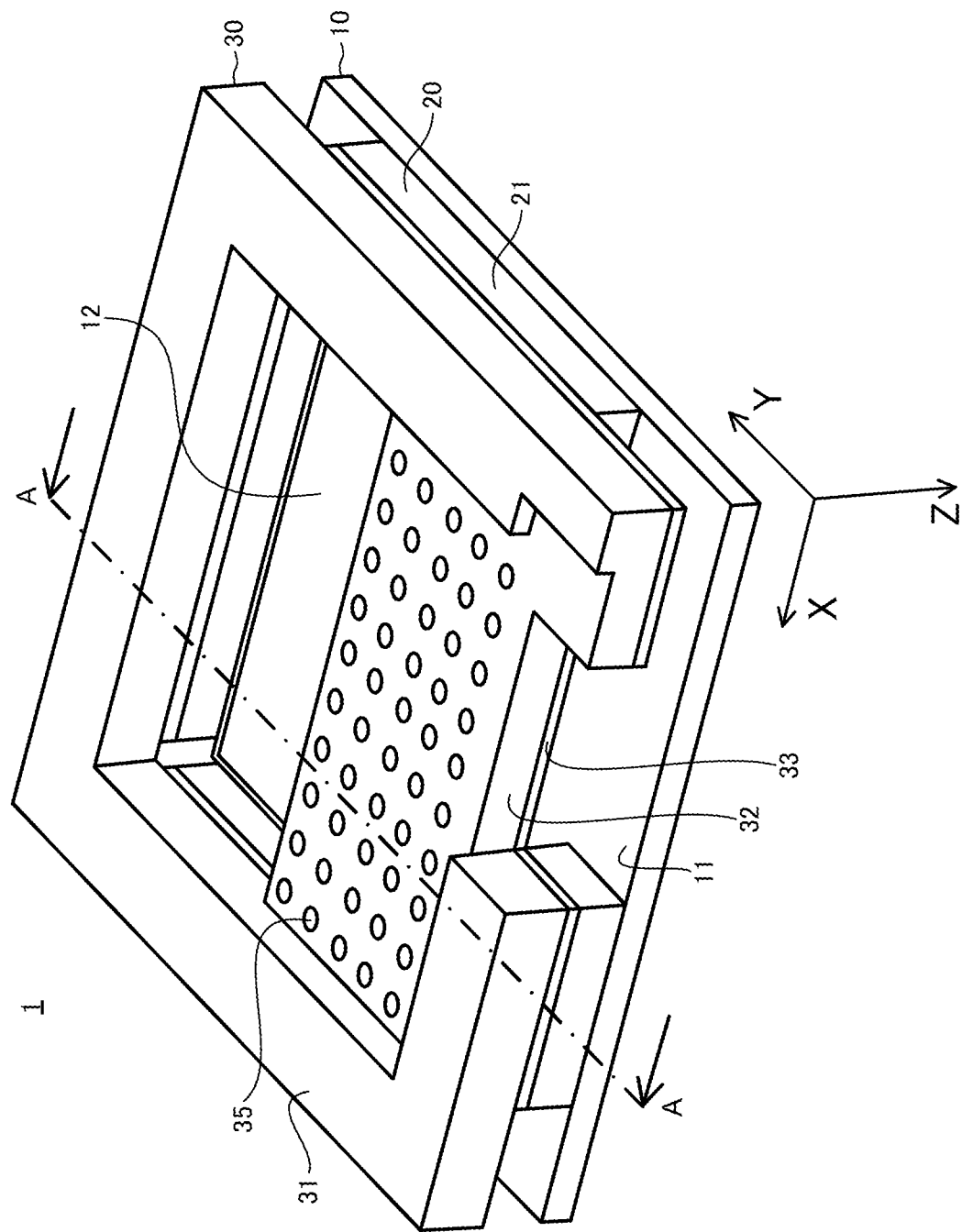
FIG. 3 is a perspective view of a detector of FIG. 2.

As illustrated in FIG. 3, the detector 1 is a sensor that detects an elastic wave propagating through air. The detector 1 detects an elastic wave by converting the elastic wave propagating through air into an electric signal. An example of the elastic wave is a sound wave or a ultrasound wave.

The detector 1 of this example is a capacitive sensor. The detector 1 may also be referred to as an acoustic transducer, a microphone, or a pressure sensor. The detector 1 may be constituted by means of Micro Electro Mechanical Systems (MEMS).

As illustrated in FIG. 3, the detector 1 has a rectangular (particularly in this example, square) plate shape. For example, the length of one side of the detector 1 is in the range of 1 mm to 10 mm. The length of one side of the detector 1 of this example is 6 mm. As illustrated in FIGS. 3 and 4, the detector 1 includes a first electrode layer 10 in a plate shape, an insulation layer 20 in a plate shape, and a second electrode layer 30 in a plate shape. FIG. 4 illustrates the cross section of the line A-A of the detector 1 of FIG. 3.

The insulation layer 20 is in contact with the first electrode layer 10. The second electrode layer 30 is in contact with the insulation layer 20 on the opposite side of the first electrode layer 10. In other words, these layers are deposited in sequence of the first electrode layer 10, the insulation layer 20, and the second electrode layer 30. Furthermore, it can be said that the insulation layer 20 is sandwiched between the first electrode layer 10 and the second electrode layer 30.

For example, the first electrode layer 10 has a thickness in the range of 1 μm to 20 μm; the insulation layer 20 has a thickness in the range of 0.1 μm to 10 μm; and the second electrode layer 30 has a thickness in the range of 10 μm to 1 mm. In this example, the first electrode layer 10 has a thickness of 7 μm; the insulation layer 20 has a thickness of 1 μm; and the second electrode layer 30 has a thickness of 300 μm.

Figure 5:
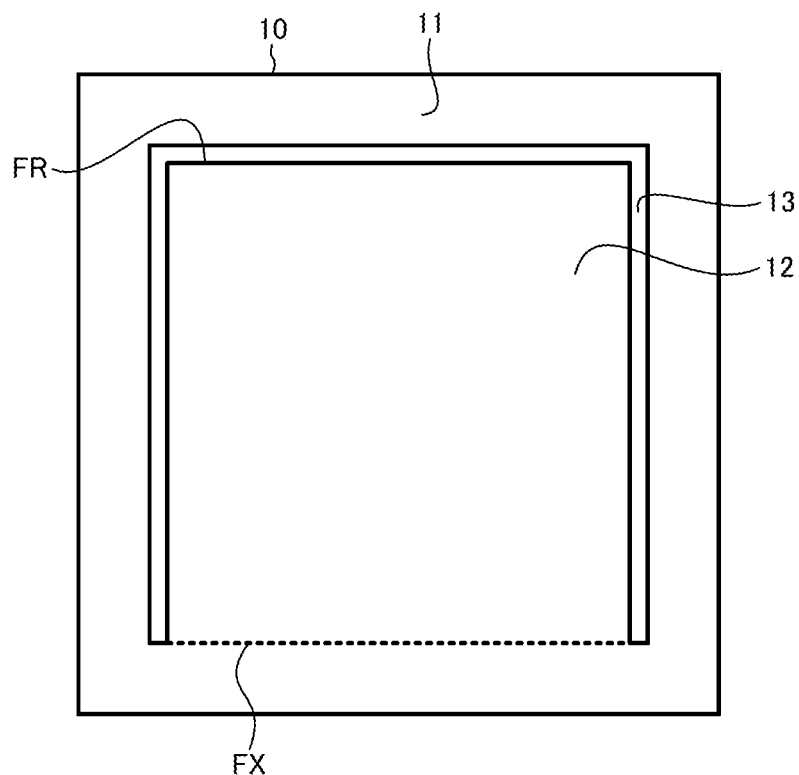
FIG. 5 is a front view of a detector of FIG. 2.

As illustrated in FIGS. 3-5, the detector 1 will now be described by using the right-handed orthogonal coordinate system having the X, Y, and Z axes. The Z axis extends along the direction perpendicular to the detector 1 (in other words, along the thickness direction of the detector 1). The positive direction of the Z axis is a direction from the second electrode layer 30 to the first electrode layer 10.

The Y axis extends in the direction from a fixed end FX to a free end FR of the first electrode 12 that is to be detailed below. The positive direction of the Y axis is a direction from the fixed end FX to the free end FR of the first electrode 12 that is to be detailed below. The X axis extends along the fixed end FX or the free end FR of the first electrode 12 that is to be detailed below.

FIGS. 9, 10, and 12-15 to be detailed below uses the same orthogonal coordinate system as FIGS. 3-5.

The first electrode layer 10 of this example is made of silicon (Si). The first electrode layer 10 includes a first support 11 and the first electrode 12.

As illustrated in FIG. 5, which is a view of the detector 1 towards the negative direction of the Z axis, the first support 11, if seen along the direction of the Z axis, has a predetermined width and also extends along the outer edge of the first electrode layer 10, so that the first support 11 forms the outer edge of the first electrode layer 10. In other words, the first support 11 has a shape of a hollow rectangular prism extending along the Z axis and having a hollow penetrating along the Z axis.

The first electrode 12, if being seen from the direction along the Z axis, has a rectangular (in this example, square) shape.

The first electrode 12 extends, in the positive direction of the Y axis, from a portion on the negative side of the Y axis of the two portions of the first support 11 extending along the direction of the X axis. In other words, the end FX, which is on the negative side of the Y axis of the first electrode 12, is coupled to a portion on the negative side of the Y axis of the two portions of the first support 11 extending along the direction of the X axis, so that the first electrode 12 is supported by the first support 11.

The first electrode 12 has a predetermined space (in other words, slit) 13 between remaining portion of the edge (in other words, the outer edge) thereof except for the end FX on the negative side of the Y axis and the first support 11. In other words, an end FX in a direction along the Y axis of the first electrode 12 is fixed on the detector 1, and the remaining portion except for the end FX is not fixed on the detector 1 (in other words, spaced apart from other element).

With this configuration, the first electrode 12 vibrates as depicted by an Arrow SA of FIG. 4 by being bent by the elastic wave. The end FX of the first electrode 12 on the negative side of the Y axis is an example of the fixed end FX while the end FR of the first electrode 12 on the positive side of the Y axis is an example of the free end FR.

This means that the first electrode 12 has a cantilever structure having the fixed end FX and the free end FR. The first electrode 12 of this example can be regarded as a Square Beam.

The insulation layer 20 is made of an insulator material. In this example, the insulation layer 20 is made of silicon dioxide ($SiO_2$). The insulation layer 20 may also be referred to as a silicon oxide layer.

As illustrated in FIG. 4, the insulation layer 20 includes an outer edge 21. The outer edge 21 has, if seen along the direction along the Z axis, a predetermined width and extends along the outer edge of the insulation layer 20 so as to form the outer edge of the insulation layer 20.

In other words, the outer edge 21 has a shape of a hollow rectangular prism extending along the Z axis and having a hollow penetrating along the Z axis. It is considered that the insulation layer 20 has a first penetrating hole 22 that opens at a portion thereof opposed to the first electrode 12 and that penetrates the insulation layer 20 along the direction of the Z axis. In this example, when the detector 1 is seen along the direction of the Z axis, the width of the outer edge 21 matches with that of the first support 11.

In this example, the second electrode layer 30 is made of silicon (Si). The second electrode layer 30 includes, a second support 31, a second electrode 32, and an electret layer 33.

The second support 31, if seen along the direction of the Z axis, has a predetermined width and extends along the outer edge of the second electrode layer 30 so as to form the outer edge. In other words, the second support 31 has a shape of a hollow rectangular prism extending along the Z axis and having a hollow penetrating along the Z axis. If the detector 1 is seen along the direction of the Z axis, the second support 31 has the same width as that of the first support 11.

The second electrode 32 has, if seen along the direction of the Z axis, a rectangular shape. The second electrode 32 has a length along the direction of the Y axis shorter than the length of the first electrode 12 along the direction of the Y axis. The end of the second electrode 32 on the positive side of the Y axis is located at a position closer to the fixed end FX than the free end FR along the direction of the Y axis. In this example, the end of the second electrode 32 on the positive side of the Y axis is located at a position in the middle of the fixed end FX and the free end FR along the direction of the Y axis.

It can be said that the second electrode layer 30 that has a second penetrating hole 34, that opens at a portion closer to the free end FR than the second electrode 32 along the direction of the Y axis of a portion of the second electrode layer 30 opposed to the first electrode 12, and that penetrates the second electrode layer 30 along the direction of the Z axis.

The second electrode 32 extends towards the positive direction of the X axis from a portion on the negative side of the X axis of the two portions of the second support 31 extending along the direction of the Y axis. In other words, the end of the second electrode 32 on the negative side of the X axis is coupled to a portion on the negative side of the X axis of the two portions of the second support 31 extending along the direction of the Y axis.

In addition, the second electrode 32 extends towards the negative direction of the X axis from a portion on the positive side of the X axis of the two portions of the second support 31 extending along the direction of the Y axis. In other words, the end of the second electrode 32 on the positive side of the X axis is coupled to a portion on the positive side of the X axis of the two portions of the second support 31 extending along the direction of the Y axis.

In other words, the both ends of the second electrode 32 along the direction of the X axis are fixed on the detector 1, so that the second electrode 32 is supported by the second support 31.

As illustrated in FIGS. 3 and 4, the second electrode 32 of this example is opposed to the first electrode 12 at a distance the same as the thickness of the insulation layer 20. In this example, the second electrode 32 has a thickness slightly thinner than the thickness of the second support 31.

As illustrated in FIG. 3, the second electrode 32 has multiple penetrating holes 35 that penetrate the second electrode 32 along the direction of the Z axis.

As illustrated in FIGS. 3 and 4, the electret layer 33 covers the surfaces of the second support 31 and the second electrode 32 on the positive side of the Z axis. The electret layer 33 is made of electret. For example, the electret layer 33 contains a polymer compound such as fluorine resin. In this example, the electret layer 33 is charged by corona discharge.

Alternatively, the detector 1 may omit the electret layer 33 and may apply a voltage between the first electrode 12 and the second electrode 32.

The detecting device 100 detects an elastic wave on the basis of a change in capacitance between the first electrode 12 and the second electrode 32. In this example, the detecting device 100 detects an elastic wave by detecting the difference in voltage between the first electrode 12 and the second electrode 32. Alternatively, the detecting device 100 may detect an elastic wave by detecting an electric current flowing between the first electrode 12 and the second electrode 32.

For example, Expression 1 represents the resonance frequency $f_0$ for the n-th order resonance of the first electrode 12. Here, the symbol n represents a natural number; the symbol L represents the length of the first electrode 12 along the Y axis; the symbol $\alpha_n$ represents a coefficient predetermined for the n-th order resonance. For example, the coefficient $\alpha_1$ may be 0.162. The symbol d represents the thickness of the first electrode 12 (in other words, the length of the first electrode 12 along the Z axis). The symbol ρ represents the density of the material of the first electrode 12. The symbol E represents the Young's modulus of the material of the first electrode 12.

$$f_0 = \alpha_n \frac{d}{L^2} \sqrt{\frac{E}{\rho}} \qquad \text{[Expression 1]}$$

For example, it is assumed that a target, when being irradiated with light having an intensity $I_0$, generates an elastic wave having a frequency f close to the resonance frequency $f_0$ of the first electrode 12. In this case, the amplitude A of the free end FR of the first electrode 12 along the direction of Z axis is expressed by Expression 2. The symbol α represents the absorption coefficient of the target. An absorption coefficient may also be referred to a light absorption coefficient. The symbol γ represents the ratio specific heat (in other words, heat capacity ratio) of the target. The symbol Q represents the Q value of the first electrode 12.

$$A = \frac{(\gamma - 1)\alpha Q I_0}{8\pi^3 f \rho d f_0^2} \qquad \text{[Expression 2]}$$

As denoted in Expression 2, a higher Q value increases the amplitude A of the first electrode 12. Consequently, the elastic wave can be precisely detected. Furthermore, according to Expression 2, a lower frequency f increases the amplitude A of the first electrode 12, so that the elastic wave can be precisely detected. In addition, according to Expression 2, a smaller thickness d of the first electrode 12 increases the amplitude A of the first electrode 12, so that the elastic wave can be precisely detected.

In this example, at least part of the detector 1 is manufactured in the process of FIGS. 6A to 6D.

Alternatively, at least part of the detector 1 may be manufactured in a process different from that of FIGS. 6A to 6D.

Figure 6A:
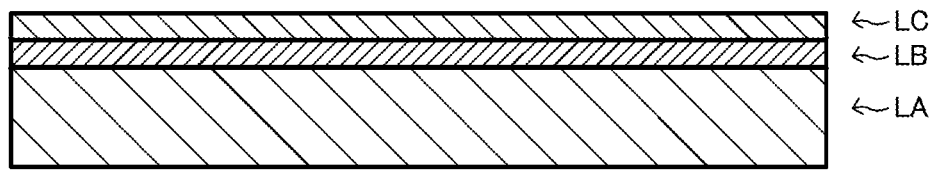
FIGS. 6A to 6D are diagrams illustrating an example of a process of manufacturing a detector of FIG. 2.

First of all, as illustrated in FIG. 6A, a Silicon On Insulator (SOI) substrate is prepared which includes a first silicone layer LA, an insulation layer LB in contact with the first silicon layer LA, and a second silicone layer LC in contact with the insulation layer LB. The insulation layer LB is made of silicon dioxide ($SiO_2$).

Figure 6B:
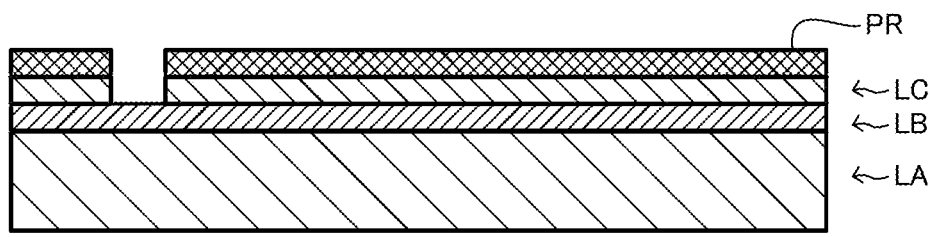

As illustrated in FIG. 6B, a photoresist layer PR having a predetermined pattern is formed on the second silicon layer LC on the opposite side of the insulation layer LB using a photolithography technique. Then, the portion from which the photoresist layer PR is absent of the second silicon layer LC is removed by using an etching technique.

Figure 6C:
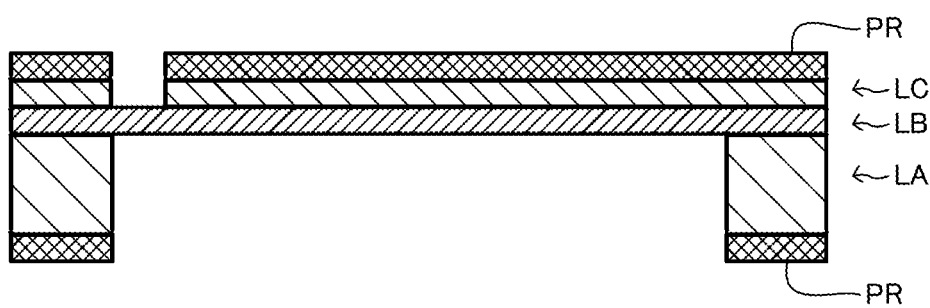

As illustrated in FIG. 6C, a photoresist layer PR having a predetermined pattern is formed on the first silicon layer LA on the opposite side of the insulation layer LB using the photolithography technique. Then, the portion from which the photoresist layer PR is absent of the first silicon layer LA is removed by using the etching technique.

Figure 6D:
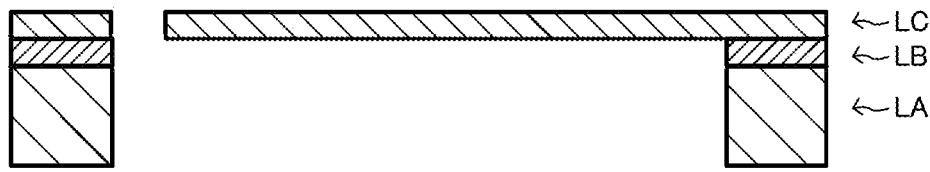

After that, as illustrated in FIG. 6D, the photoresist layers PR are removed. Further, using the etching technique including critical point drying (in other words, supercritical drying), the portion of the insulation layer LB not being in contact with the first silicon layer LA is removed.

At least part of the detector 1 is manufactured in the above process. For example, the first electrode layer 10 and the second electrode layer 30 may be manufactured in the process of FIGS. 6A to 6D.

Figure 7:
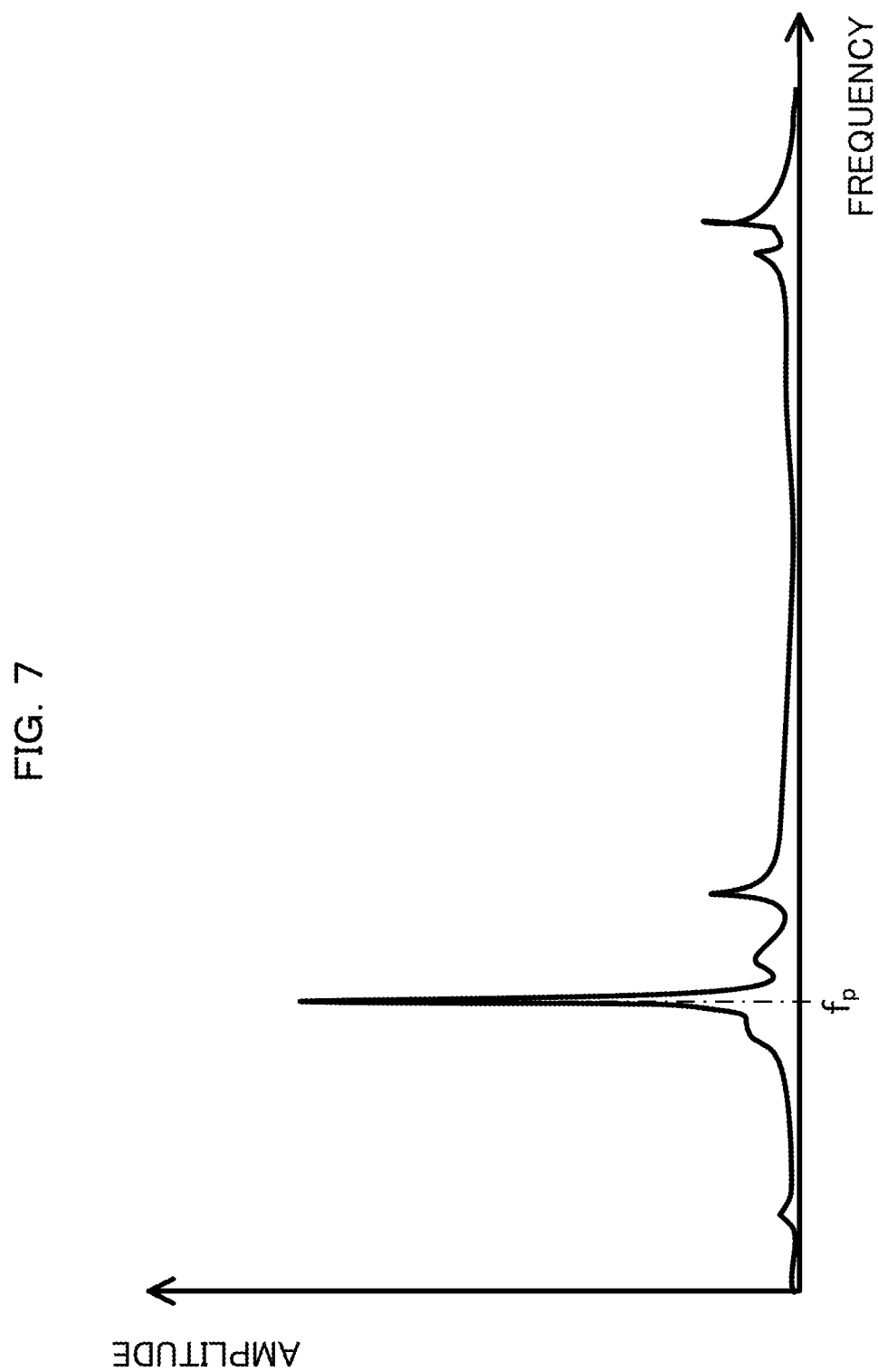
FIG. 7 is a graph depicting an example of a change of the amplitude of electric potential difference between electrodes in terms of the frequency of an elastic wave when the elastic wave arrives at a detector of FIG. 2.

FIG. 7 depicts a change in amplitude of the electric potential difference between the first electrode 12 and the second electrode 32 in terms of the frequency of an elastic wave when the elastic wave arrives at the detector 1. As illustrated in FIG. 7, the amplitude changes in terms of a frequency so as to have a sharp peak at a particular frequency $f_p$. The result of measuring the properties of the detector 1 revealed that the detector 1 has a Q value of about 104, a sensitivity of 16 dB, a Signal to Noise ratio (SN ratio) of 42 dB. This means that the detector 1 is capable of precisely detecting an elastic wave having a particular frequency.

(Operation)

Next, the operation of the detecting device 100 will now be detailed.

First of all, the light source 2 generates laser light having the frequency for the oscillation period each time the oscillation cycle elapses. A living body is irradiated with the laser light generated by the light source 2. The target in the living body generates an elastic wave having a frequency corresponding to the oscillation cycle in response to the laser light. The generated elastic wave propagates through the air and finally arrives at the first electrode 12. Thereby, the first electrode 12 responsively vibrates in the direction along the Z axis.

Consequently, the capacitance between the first electrode 12 and the second electrode 32 changes to accompany a change in electric potential difference between the first electrode 12 and the second electrode 32. In this example, the oscillation cycle is set to correspond to the resonance frequency $f_0$ of the first electrode 12. Accordingly, the elastic wave generated in response to the laser light, with which the target is irradiated, has a frequency close to the resonance frequency $f_0$ of the first electrode 12. This vibrates the first electrode 12 at a frequency close to the resonance frequency $f_0$ of the first electrode 12.

Accordingly, the electric potential difference between the first electrode 12 and the second electrode 32 vibrates at a frequency close to the resonance frequency $f_0$ of the first electrode 12. The detecting device 100 detects an elastic wave by detecting the vibration of the electric potential difference between the first electrode 12 and the second electrode 32, so that the detecting device 100 detects the target in the living body.

As described above, the first electrode 12 of the detecting device 100 of the first embodiment has a cantilever structure with the fixed end FX and the free end FR and also has a plate shape that vibrates by being bent by an elastic wave. Furthermore, the second electrode 32 has a plate shape opposed to the first electrode 12 at a predetermined distance. In addition, the detecting device 100 detects an elastic wave on the basis of a change in capacitance between the first electrode 12 and the second electrode 32. The end of the second electrode 32 in the direction from the fixed end FX to the free end FR is located at a position closer to the fixed end FX than the free end FR.

This means that the second electrode 32 is absent from a position opposed to the free end FR of the first electrode 12. This can suppress the extent of attenuating the vibration of the first electrode 12, which attenuating is caused by the air between the first electrode 12 and the second electrode 32, so that the elastic wave can be precisely detected.

Here, when a target is to be detected by using the photoacoustic effect, the target generates an elastic wave having a particular frequency. This means that there is possibility of failing in precisely detecting the target unless the detection uses a detecting device capable of precisely detecting an elastic wave having a particular frequency.

In contrast to the above, the detecting device 100 produces resonance of the first electrode 12 when an elastic wave having a frequency close to the resonance frequency of the first electrode 12 arrives at the first electrode 12. Advantageously, the detecting device 100 is capable of precisely detecting an elastic wave having a frequency close to the resonance frequency of the first electrode 12. This allows the detecting device 100 to precisely detect a target in the living body using the photoacoustic effect.

Further, in the detecting device 100, the second electrode layer 30 has the second penetrating hole 34 at a portion closer to the free end FR than the second electrode 32 in the direction from the fixed end FX to the free end FR within a portion of the second electrode layer 30 opposed to the first electrode 12.

This means that the second penetrating hole 34 is disposed at a position opposed to the free end FR of the first electrode 12. This can suppress the extent of attenuating the vibration of the first electrode 12, which attenuating is caused by the air between the first electrode layer 10 and the second electrode layer 30, so that the elastic wave can be precisely detected.

Furthermore, the second electrode 32 of the detecting device 100 of the first embodiment includes multiple penetrating holes 35.

This can suppress the extent of attenuating the vibration of the first electrode 12, which attenuating is caused by the air between the first electrode 12 and the second electrode 32, so that the elastic wave can be precisely detected.

Figure 8:
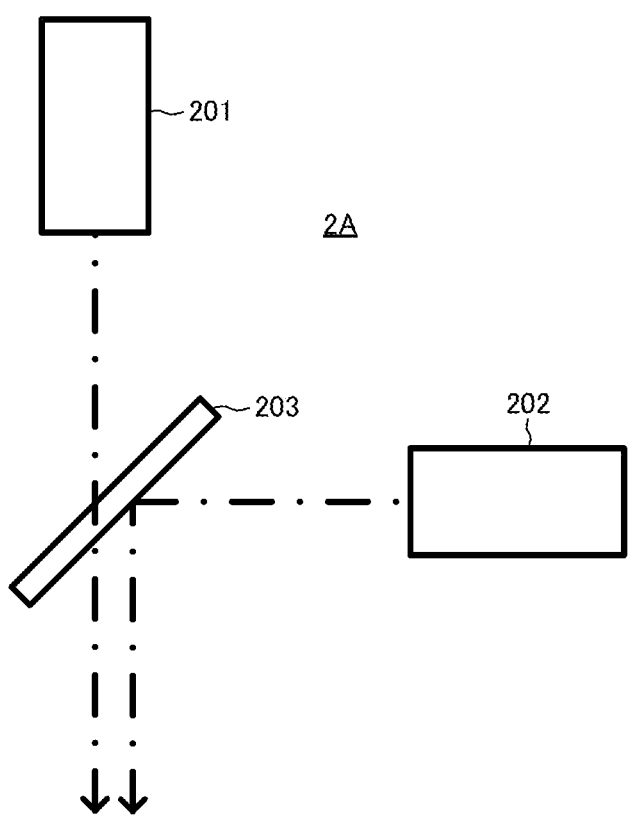
FIG. 8 is a block diagram illustrating a modification to a light source of FIG. 2.

As illustrated in FIG. 8, the detecting device 100 may include a light source 2A generating multiple laser light beams having respective different wavelengths in place of the light source 2. The light source 2A includes a first light generator 201, a second light generator 202, and a halfmirror 203. The light source 2A may include three or more light generators.

The first light generator 201 generates a laser light beam having a first wavelength while the second light generator 202 generates a laser light beam having a second wavelength different from the first wavelength. The halfmirror 203 passes the light having the first wavelength and reflects the light having the second wavelength.

This configuration allows the light source 2A to irradiate the same position with the laser light beam having the first wavelength and the laser light beam having the second wavelength. The detecting device 100 detects two elastic waves generated by irradiation with the two laser light beams, and detects an elastic wave generated by a predetermined target on the basis of the result of the detection.

The intensity of an elastic wave that an article generates in response to being irradiated with light changes with the wavelength of the light. Consequently, this modification can remove a component of an elastic wave generated by an article except for the target from the detected elastic wave, so that the target can be precisely detected.

For example, assuming that a target generates, when being irradiated with the light having the first wavelength, an elastic wave having a larger intensity than that of an elastic wave that the target generates when being irradiated with the light having the second wavelength, the detecting device 100 may detect an elastic wave generated by the target on the basis of a difference obtained by subtracting the result of detecting of an elastic wave for the second wavelength from the result of detecting of an elastic wave for the first wavelength.

The detecting device 100 may detect a target included in an article except for a living body. For example, the detecting device 100 may be used in a flaw detection test that detects flaw or defect in a device, a part, or a structure. The flaw detection test may also be referred to as a flaw detecting inspection or a non-destructive inspection. Alternatively, the detecting device 100 may be used for water quality examination that detects a component such as a mineral and a bacterium contained in water. The detecting device 100 may be applied to food inspection that detects water, vitamin, mineral, salt, sugar, or additive contained in food. In addition, the detecting device 100 may be used as a gas sensor that detects a component such as water vapor or carbon dioxide contained in gas.

The detector 1 may be applied to a detecting device not using the photoacoustic effect.

First Modification to First Embodiment

Here, description will now be made in relation to a detecting device according to a first modification to the first embodiment. The detecting device of the first modification to the first embodiment is different from the detecting device of the first embodiment in the shape of the first electrode. Hereinafter, the description focuses on the difference of the first modification to the first embodiment from the first embodiment. Like reference numbers designate the same or similar parts and elements both in the first embodiment and the first modification thereof.

Figure 9:
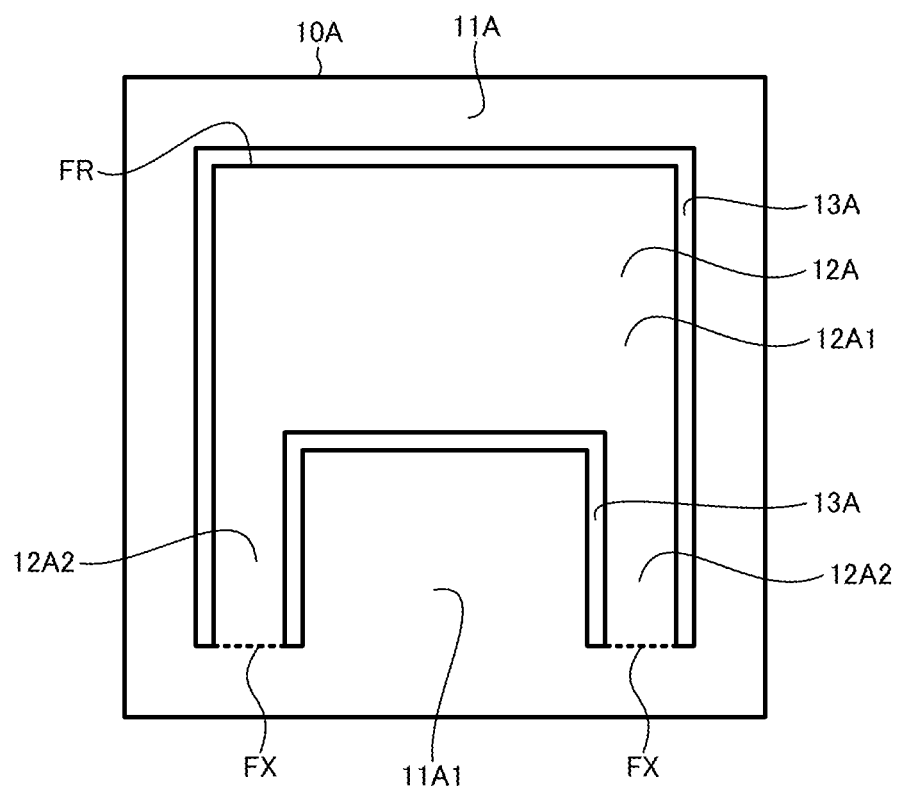
FIG. 9 is a front view of a detector according to a first modification to the first embodiment.

As illustrated in FIG. 9, the detector 1 of the first modification to the first embodiment includes a first electrode layer 10A in place of the first electrode layer 10 of the first embodiment.

The first electrode layer 10A includes a first support 11A and a first electrode 12A. The first electrode 12A includes a body 12A1 and two legs 12A2.

The first support 11A, if seen along the direction of the Z axis, has a predetermined width and extends along the outer edge so as to form the outer edge of the first electrode layer 10A. In other words, the first support 11A has a shape of a hollow rectangular prism extending along the Z axis and having a hollow penetrating along the Z axis.

A portion on the negative side of the Y axis of the two portions of the first support 11A extending along the direction of the X axis has a wider portion 11A1 at a center portion along the direction of the X axis. The wider portion 11A1 is wider than the remaining portion of the first support 11A seen along the direction of the Z axis.

The body 12A1, if the first electrode 12A is seen along a direction of the Z axis, has a rectangular shape having longer sides extending along the direction of the X axis and shorter sides extending along the direction of the Y axis. The two legs 12A2 extend in the negative direction of the Y axis from the end portions along the direction of the X axis on the end of the body 12A1 on the negative side of the Y axis. Furthermore, the two legs 12A2 extend in the positive direction of the Y axis from the portion on the negative side of the Y axis of the two portions of the first support 11A extending along the direction of the X axis.

In other words, the end FX of each leg 12A2 on the negative side of the Y axis is coupled to the portion on the negative side of the Y axis of the two portions of the first support 11A extending along the direction of the X axis. Accordingly, the first electrode 12A is supported by the first support 11A.

The first electrode 12A has a predetermined space (in other words, slit) 13A between remaining portion of the edge (in other words, the outer edge) of the first electrode 12A except for the ends FX of the first electrode 12A on the negative side of the Y axis and the first support 11A. In other words, the first electrode 12A has ends FX on the negative side of the Y axis being fixed on the detector 1 and the remaining portion except for the ends FX not being fixed on the detector 1 (in other words, being spaced apart from other element).

With this configuration, the first electrode 12A vibrates by being bent by the elastic wave. Each of the ends FX of the first electrode 12A on the negative side of the Y axis is an example of the fixed end FX while the end FR of the first electrode 12A on the positive side of the Y axis is an example of the free end FR.

This means that the first electrode 12A has a cantilever structure having the fixed end FX and the free end FR. The first electrode 12A of this example can be regarded as a Long Leg Beam.

The detecting device 100 of the first modification to the first embodiment ensures the same effects and advantages as those of the detecting device 100 of the first embodiment.

Second Modification to First Modification

Here, description will now be made in relation to a detecting device according to a second modification to the first embodiment. The detecting device of the second modification to the first embodiment is different from the detecting device of the first embodiment in the shape of the first electrode. Hereinafter, the description focuses on the difference of the second modification to the first embodiment from the first embodiment. Like reference numbers designate the same or similar parts and elements both in the first embodiment and the second modification thereof.

As illustrated in FIG. 10, the detector 1 of the second modification to the first embodiment includes a first electrode layer 10B in place of the first electrode layer 10 of the first embodiment.

The first electrode layer 10B includes a first support 11B and a first electrode 12B. The first electrode 12B includes a body 12B1, a first leg 12B2, and a second leg 12B3.

The first support 11B, if seen along the direction of the Z axis, has a predetermined width and extends along the outer edge so as to form the outer edge of the first electrode layer 10B. In other words, the first support 11B has a shape of a hollow rectangular prism extending along the Z axis and having a hollow penetrating along the Z axis.

Each of the two portions of the first support 11B extending along the direction of the Y axis has a wider portion 11B1 at a portion except for the end portion on the negative side of the Y axis. The wider portion 11B1 is wider than the remaining portion of the first support 11B seen along the direction of the Z axis.

The body 12B1, if the first electrode 12B is seen along the direction of the Z axis, has a rectangular shape having longer sides extending along the direction of the Y axis and shorter sides extending along the direction of the X axis.

The first leg 12B2 extends in the negative direction of the X axis from the end portion on the negative side of the Y axis of the body 12B1 of the end of the body 12B1 on the negative side of the X axis. In addition, the first leg 12B2 extends in the positive direction of the X axis from a portion on the negative side of the X axis of the two portions of the first support 11B extending along the direction of the Y axis. In other words, the end FX of the first leg 12B2 on the negative side of the X axis is coupled to the portion on the negative side of the X axis of the two portions of the first support 11B extending along the direction of the Y axis.

The second leg 12B3 extends in the positive direction of the X axis from the end portion on the negative side of the Y axis of the end of the body 12B1 on the positive side of the X axis. In addition, the second leg 12B3 extends in the negative direction of the X axis from a portion on the positive side of the X axis of the two portions of the first support 11B extending along the direction of the Y axis. In other words, the end FX of the second leg 12B3 on the positive side of the X axis is coupled to the portion on the positive side of the X axis of the two portions of the first support 11B extending along the direction of the Y axis.

With this configuration, the first electrode 12B is supported by the first support 11B.

The first electrode 12B has a predetermined space (in other words, slit) 13B between remaining portion except for the end portions FX on the negative side of the Y axis of the both ends along the direction of the X axis of the edge (in other words, the outer edge) of the first electrode 12B and the first support 11B. In other words, the first electrode 12B has end portions FX along the direction of the Y axis being coupled to the detector 1 and the remaining portion except for the end portions FX not being coupled to the detector 1 (in other words, being apart from other element).

With this configuration, the first electrode 12B vibrates by being bent by the elastic wave. Each of the end portions FX of the first electrode 12B on the negative side of the Y axis is an example of the fixed end FX while the end FR of the first electrode 12B on the positive side of the Y axis is an example of the free end FR.

This means that the first electrode 12B has a cantilever structure with the fixed end FX and the free end FR. The first electrode 12B of this example can be regarded as a Torsion Beam.

The detecting device 100 of the second modification to the first embodiment ensures the same effects and advantages as those of the detecting device 100 of the first embodiment.

Second Embodiment

Next, description will now be made in relation to a detecting device according to a second embodiment. The detecting device of the second embodiment is different from the detecting device of the first embodiment in the point of having a space to resonate air by an elastic wave. Hereinafter, the description focuses on the difference of the second embodiment from the first embodiment. Like reference numbers designate the same or similar parts and elements both in the first embodiment and the second embodiment.

Figure 11:
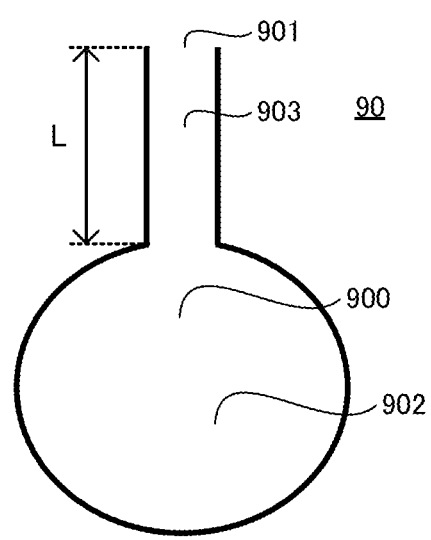
FIG. 11 is a diagram illustrating an example of Helmholtz resonance.

First, description will now be made in relation to Helmholtz resonance in a vessel 90 illustrated in FIG. 11. The vessel 90 has a space 900 (inner space) thereof and an opening 901 communicated with the space 900. The space 900 includes a base 902 and a pipe 903 that communicates the base 902 with the opening 901.

The base 902 has a volume V. The pipe 903 has a pillar shape whose cross section has an area S and a length L. In this example, the volume LS of the pipe 903 is sufficiently smaller than the volume V of the base 902.

Since the air in the base 902 functions as a spring, the air in the pipe 903 can be regarded as a rigid body and also a piston having a mass of $\rho SL$ and making reciprocating motion in the pipe 903. The symbol $\rho$ represents the density of air. Accordingly, the natural angular frequency $\omega_0$ in the space 900 is expressed by Expression 3.

$$\omega_0 = c\sqrt{\frac{S}{VL}} \qquad \text{[Expression 3]}$$

As denoted in Expression 4, the symbol c represents the velocity of sound; the symbol γ represents the ratio of specific heat of air; and the symbol p represents the pressure of air.

$$c \sqrt{\frac{\gamma p}{\rho}}$$ [Expression 4]

Accordingly, an elastic wave having a frequency corresponding to the natural angular frequency $\omega_0$ arrives at a position close to the opening 901, the air in the space 900 resonances. The resonance of the air in space 900 by an elastic wave having a frequency corresponding to the natural angular frequency $\omega_0$ may be referred to Helmholtz resonance.

The detecting device of the second embodiment detects a target in a living body using Helmholtz resonance.

Figure 12:
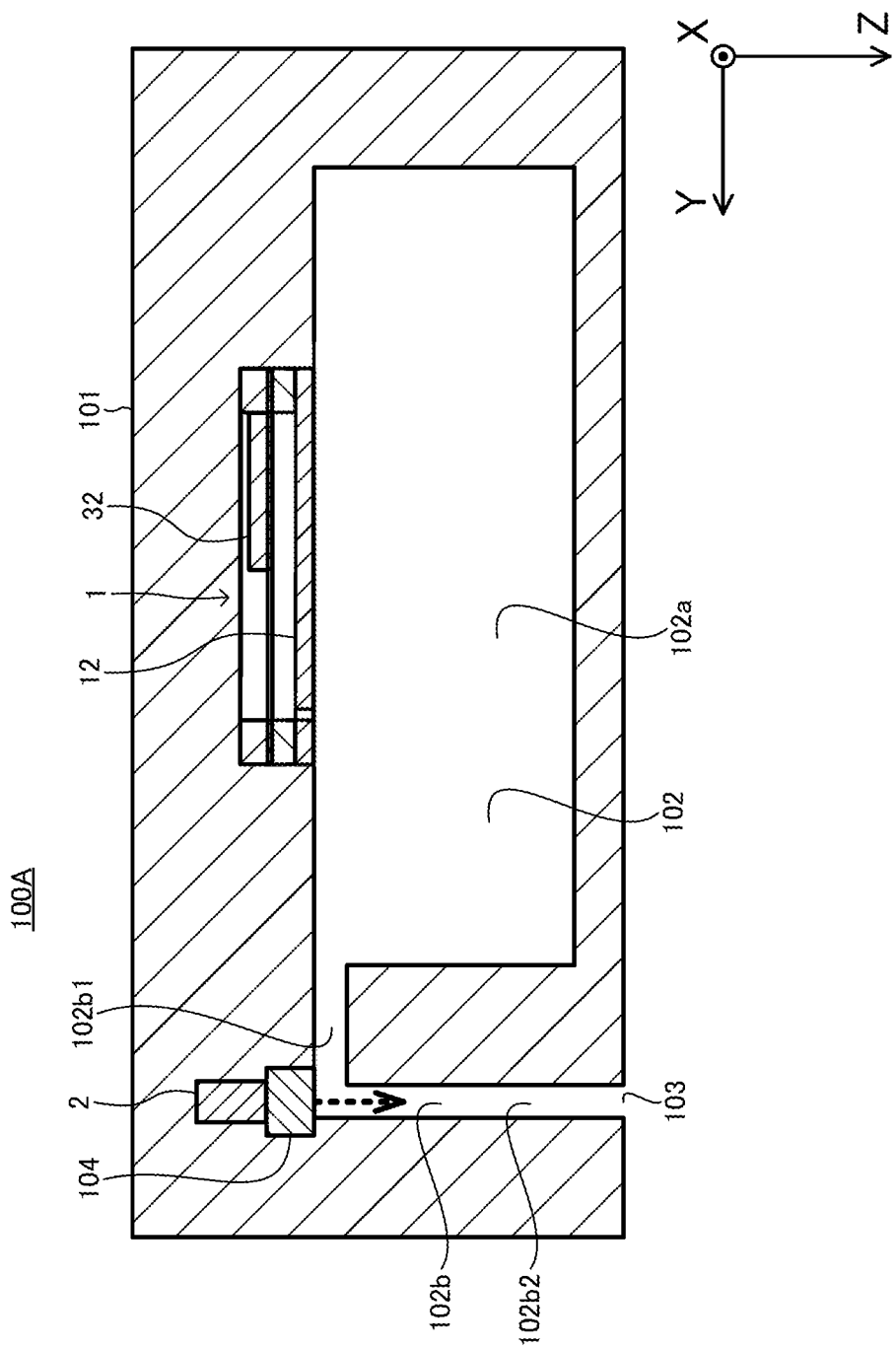
FIG. 12 is a sectional view of a detecting device according to a second embodiment.

As illustrated in FIG. 12, the detecting device 100A of the second embodiment includes a body 101, a detector 1, and a light source 2.

The body 101 has an inner space 102 and an opening 103 communicated with the inner space 102. The end on the positive side of the Z axis of the body 101 has a plate shape. The opening 103 is located at the edge face on the positive side of the Z axis of the body 101.

The inner space 102 includes a base 102a and a pipe 102b that communicates the base 102a with the opening 103.

In this example, the base 102a has a shape of a rectangular parallelepiped (in other words, cuboid) having two faces perpendicular to each of the X axis, the Y axis, and the Z axis. For example, the base 102a has a length along each of the X axis, the Y axis, and the Z axis in the range of 1 mm to 100 mm.

The pipe 102b includes a first pipe 102b1 and a second pipe 102b2. In this example, the first pipe 102b1 and the second pipe 102b2 both have circular cross sections. For example, the diameters of the respective cross sections of the first pipe 102b1 and the second pipe 102b2 are in the range of 0.1 mm to 10 mm. For example, the pipe 102b has a length in the range of 1 mm to 100 mm. Alternatively, the cross sections of the first pipe 102b1 and the second pipe 102b2 may be different shapes (e.g., a rectangular shape) from a circular shape.

The first pipe 102b1 extends in the positive direction of the Y axis from the position at the end portion of the base 102a on the negative side of the Z axis and also at the end of the base 102a on the positive side of the Y axis. The second pipe 102b2 extends from the end portion of the first pipe 102b1 on the positive side of the Y axis in the positive direction of the Z axis. In other words, the first pipe 102b1 communicates the base 102a and the second pipe 102b2. The second pipe 102b2 communicates with the first pipe 102b1 with the opening 103.

The detector 1 is embedded in a wall forming the base 102a of the body 101 in such a manner that the first electrode layer 10 is in contact with the base 102a. Consequently, the detector 1 is fixed on the body 101. In this example, the detector 1 is located on a wall forming the end face on the negative side of the Z axis of the base 102a.

The body 101 has, in a wall forming the pipe 102b, a vent 104 through which light passes. Specifically, the vent 104 is located on the wall forming the end portion on the negative side of the Z axis of the pipe 102b. In other words, the vent 104 is located on the same side as the detector 1 with respect to the inner space 102 along the direction of the Z axis. The vent 104 of this example is in contact with a portion connecting between the first pipe 102b1 and the second pipe 102b2 of the pipe 102b. This means that the vent 104 is located on the straight line extending along the second pipe 102b2. The second pipe 102b2 extends along the straight line connecting the vent 104 and the opening 103. The vent 104 of this example is made of a material that allows light to pass through. The vent 104 may be an opening.

The light source 2 is fixed on the body 101 such that the opening 103 of the body 101 is irradiated with the laser light generated by the light source 2 through the vent 104 and the second pipe 102b2. The light source 2 of this example is located on the negative side of the Z axis with respect to the vent 104.

The body 101 has a shape such that the resonance frequency of the Helmholtz resonance in the inner space 102 matches with the resonance frequency of the first electrode 12. Alternatively, the shape of the inner space 102 may be different from that of the above example. The body 101 is an example of the Helmholtz resonator.

(Operation)

Next, description will now be made in relation to the operation of the detecting device 100A.

For example, at least one of a living body and the detecting device 100A is moved such that the living body closes the opening 103. The living body does not have to close the opening 103.

First of all, the light source 2 generates laser light having the frequency for the oscillation period each time the oscillation cycle elapses. The living body is irradiated with the laser light generated by the light source 2 through the vent 104 and the second pipe 102b2. The target in the living body generates an elastic wave having a frequency corresponding to the oscillation cycle in response to the laser light. The generated elastic wave resonates the air in the inner space 102.

The air resonated in the inner space 102 arrives at the first electrode 12, being in the form of an elastic wave, so that the first electrode 12 vibrates along the direction of the Z axis.

The vibration changes the capacitance between the first electrode 12 and the second electrode 32, which leads to a change in electric potential difference between the first electrode 12 and the second electrode 32. In this example, the oscillation cycle is set to a cycle corresponding to the resonance frequency $f_0$ of the first electrode 12. The frequency of the elastic wave generated in response to the laser light, with which the target is irradiated, has a frequency close to the resonance frequency $f_0$ of the first electrode 12. This vibrates the first electrode 12 at a frequency close to the resonance frequency $f_0$ of the first electrode 12.

Accordingly, the electric potential difference between the first electrode 12 and the second electrode 32 vibrates at a frequency close to the resonance frequency $f_0$ of the first electrode 12. The detecting device 100A detects an elastic wave by detecting the vibration of the electric potential difference between the first electrode 12 and the second electrode 32, so that the detecting device 100A detects the target in the living body.

As described above, the detecting device 100A of the second embodiment brings the same effects and advantages as those of the detecting device 100 of the first embodiment.

Furthermore, in the detecting device 100A of the second embodiment, the body 101 has the inner space 102 being in contact with the detector 1 and also has the opening 103 communicated with the inner space 102.

With this configuration, the air in the inner space 102 of the body 101 can be resonated by an elastic wave having a particular frequency. Consequently, the detecting device 100A can precisely detect the elastic wave having the particular frequency.

In addition, the detecting device 100A of the second embodiment has the vent 104 through which the light generated by the light source 2 passes.

With this configuration, the target is irradiated through the opening 103 with the light that enters from the vent 104 and the elastic wave generated by the target can be detected by the detector 1. Accordingly, even when the detecting device 100A is moved, since the positional relationship between a position irradiated with light and the position of the detector 1 can be maintained, the elastic wave can be precisely detected. Consequently, the target can be precisely detected.

Besides, in the detecting device 100A of the second embodiment, the vent 104 is located on the same side as the detector 1 with respect to the inner space 102.

The light source 2 is disposed in the vicinity of the vent 104. This allows the detecting device 100A to arrange the detector 1 on the same side as the light source 2 with respect to the inner space 102. This configuration can reduce the size of the detecting device 100A as compared with the case where the detector 1 is disposed on a different side from the light source 2 with respect to the inner space 102.

Furthermore, in the detecting device 100A of the second embodiment, the inner space 102 includes the base 102a and the pipe 102b that communicates the base 102a with the opening 103, and the second pipe 102b2 being part of the pipe 102b extends along the straight line connecting the vent 104 with the opening 103.

This configuration allows the second pipe 102b2 of the pipe 102b used for Helmholtz resonance to be used also as a light path through which the laser light generated by the light source 2 passes. Accordingly, there is no need to provide a light path through which the laser light generated by the light source 2 passes at a different position from the pipe 102b of the body 101, so that the size of the detecting device 100A can be reduced.

Furthermore, in the detecting device 100A of the second embodiment, the body 101 has a shape such that the resonance frequency of the Helmholtz resonance in the inner space 102 matches with the resonance frequency of the first electrode 12.

With this configuration, an elastic wave having a frequency the same as the resonance frequency of the first electrode 12 resonates the air in the inner space 102 of the body 101. Consequently, the elastic wave having a frequency the same as the resonance frequency of the first electrode 12 can be precisely detected.

The detecting device 100A may include, in place of the detector 1, a diaphragm having a cantilever structure and a piezoelectric element that detects deformation of the diaphragm, and may further include a detector that detects an elastic wave on the basis of deformation of the diaphragm. Alternatively, the detecting device 100A may include, in place of the detector 1, a diaphragm having a cantilever structure, a light source generating a laser light to irradiate the diaphragm, and multiple light detectors that detect a change in direction of reflection of the laser light from the diaphragm by detecting the laser light reflected from the diaphragm at each of multiple positions, and may also include a detector that detects an elastic wave on the basis of a change in direction of reflection of the laser light reflected from the diaphragm.

First Modification to Second Embodiment

Here, description will now be made in relation to a detecting device according to a first modification to the second embodiment. The detecting device of the first modification to the second embodiment is different from the detecting device of the second embodiment in the point of vibrating the wall that forms a space to be used for Helmholtz resonance. Hereinafter, description will focus on the difference of the detecting device of the first modification to the second embodiment from that of the second embodiment. Like reference numbers designate the same or similar parts and elements between the second embodiment and the first modification thereof.

Figure 13:
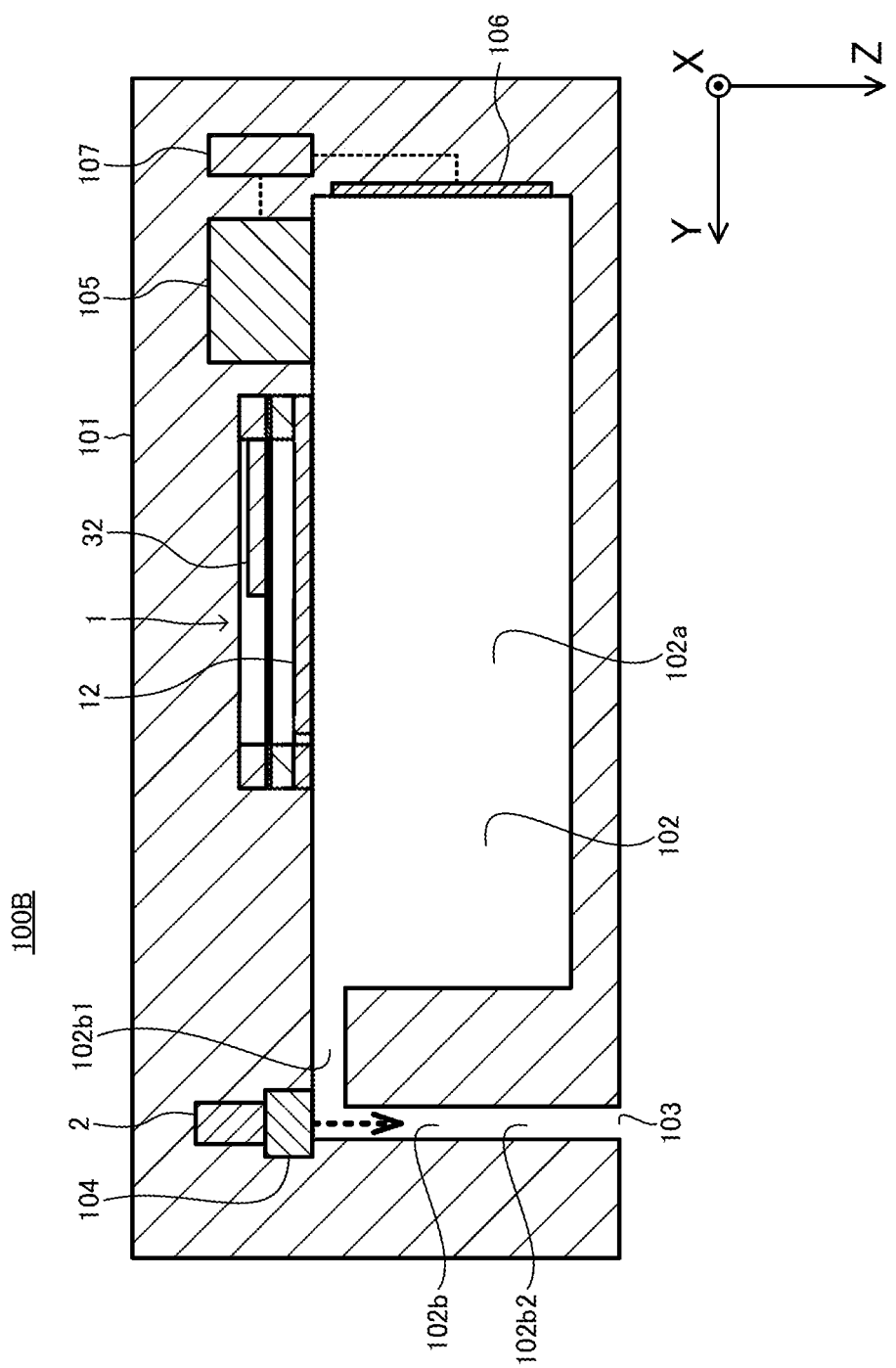
FIG. 13 is a sectional view of a detecting device according to a first modification to the second embodiment.

As illustrated in FIG. 13, a detecting device 100B of the first modification to the second embodiment includes a detector 105, a diaphragm 106, and a vibration controller 107 in addition to the elements in the detecting device 100A of the second embodiment.

The detector 105 is a sensor that detects an elastic wave propagating through the air. In this example, the detector 105 has a frequency band of a detectable elastic wave wider than that for the detector 1. Furthermore, the detector 105 has a quicker response of detecting an elastic wave than the detector 1. An example of the detector 105 is a capacitive sensor having a diaphragm structure.

The detector 105 is embedded in a wall forming the base 102a of the body 101 so as to be in contact with the base 102a. Consequently, the detector 105 is fixed on the body 101. In this example, the detector 105 is located on the wall forming the end face on the negative side of the Z axis of the base 102a.

The diaphragm 106 is vibratably embedded in the wall forming the base 102a of the body 101 so as to be in contact with the base 102a. In this example, the diaphragm 106 is located on the wall forming the end face on the negative side of the Y axis of the base 102a. The diaphragm 106 includes an actuator, which causes the diaphragm 106 to vibrate. The actuator of this example is a piezoelectric actuator, but may alternatively be of another type (such as an electromagnetic actuator).

The vibration controller 107 controls the vibration of the diaphragm 106 on the basis of a result of the detection by the detector 105. The vibration controller 107 of this example removes noise from a signal detected by the detector 105 with a filter (e.g., a low-pass filter), adjusts the amplitude and the phase of a signal subjected to the removal, and outputs the adjusted signal as a driving signal to the actuator.

The control of the vibration of the diaphragm 106 by the vibration controller 107 may be referred to as feedback control. Specifically, the vibration controller 107 of this example adjusts the amplitude in order to suppress oscillation caused by the feedback control. For example, the total of the gain in the feedback control may be set to be one or less. In addition, the vibration controller 107 may adjust the phase such that the phase of the driving signal lags 90 degrees behind the phase of the signal detected by the detector 105.

The above feedback control amplifies the resonance of the air in the inner space 102 of the body 101. In this example, the feedback control can be regarded as electromechanical active control on the Q value of a Helmholtz resonator.

As described above, the detecting device 100B of the first modification to the second embodiment brings the same effects and advantages as those of the detecting device 100A of the second embodiment.

Furthermore, in the detecting device 100B of the first modification of the second embodiment, the body 101 includes the diaphragm 106 vibratably provided on the wall forming the inner space 102. The detecting device 100B further includes the second detector 105 that has a frequency band of a detectable elastic wave wider than that for the detector 1 serving as a first detector, that detects an elastic wave propagating through air, and that is in contact with the inner space 102. In addition, the detecting device 100B further includes the vibration controller 107 that controls the vibration of the diaphragm 106 on the basis of the result of the detecting by the second detector 105.

This configuration can amplify the resonance of the air in the inner space 102 of the body 101. Consequently, an elastic wave having a particular frequency can be detected more precisely.

Alternatively, the detecting device 100B may omit the detector 105 and control the vibration of the diaphragm 106 on the basis of the result of the detection by the detector 1.

Second Modification to Second Embodiment

Here, description will now be made in relation to a detecting device according to a second modification to the second embodiment. The detecting device of the second modification to the second embodiment is different from the detecting device of the second embodiment in the point of changing a position irradiated with laser light.

Hereinafter, description will focus on the difference of the detecting device of the second modification to the second embodiment from that of the second embodiment. Like reference numbers designate the same or similar parts and elements between the second embodiment and the second modification thereof.

Figure 14:
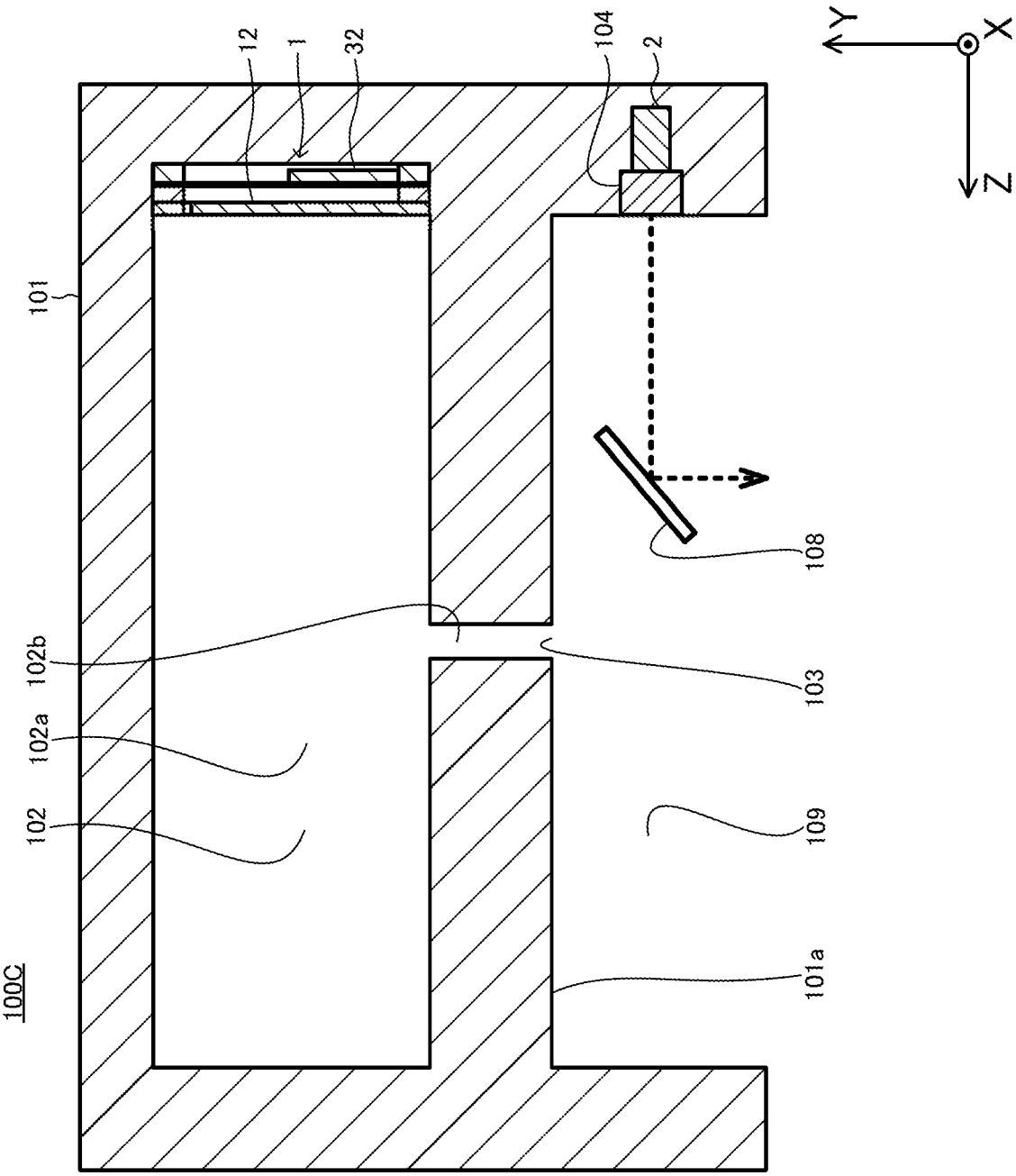
FIG. 14 is a sectional view of a detecting device according to a second modification to the second embodiment.

As illustrated in FIG. 14, a detecting device 100C of the second modification to the second embodiment includes an irradiation controller 108 in addition to the configuration of the detecting device 100A of the second embodiment.

The body 101 of the second modification to the second embodiment includes a first inner space 102 inside thereof and an opening 103 communicated with the first inner space 102. The body 101 includes a recess 101*a* at the end on the negative side of the Y axis. The opening 103 is located at the center of the recess 101*a*.

The recess 101*a* defines a second space 109. In this example, the second space 109 has a shape of a rectangular parallelepiped having two faces perpendicular to each of the X axis, the Y axis, and the Z axis. For example, the second space 109 has a length along each of the X axis, the Y axis, and the Z axis in the range of 1 mm to 100 mm.

The first inner space 102 includes a base 102*a* and a pipe 102*b*. The base 102*a* of this example has a shape of a rectangular parallelepiped having two faces perpendicular to each of the X axis, the Y axis, and the Z axis. For example, the base 102*a* has a length along each of the X axis, the Y axis, and the Z axis in the range of 1 mm to 100 mm.

In this example, the pipe 102*b* has a circular cross section. For example, the diameter of the cross section of the pipe 102*b* is in the range of 0.1 mm to 10 mm. For example, the pipe 102*b* has a length in the range of 1 mm to 100 mm. The cross section of the pipe 102*b* may be a different shape (e.g., a rectangular shape) from a circular shape.

The pipe 102*b* extends from the center of the end face on the negative side of the Y axis of the base 102*a* in the negative direction of the Y axis. The pipe 102*b* communicates the base 102*a* with the opening 103.

The detector 1 is embedded in a wall forming the base 102*a* of the body 101 such that the first electrode layer 10 is in contact with the base 102*a*. Consequently, the detector 1 is fixed on the body 101. In this example, the detector 1 is located on the wall forming the end face on the negative side of the Z axis of the base 102*a*.

The body 101 has, on the recess 101*a*, a vent 104 through which light passes. Specifically, the vent 104 is located on the wall forming the end face on the negative side of the Z axis of the second space 109. In other words, the vent 104 is located on the same side as the detector 1 with respect to the inner space 102 along the direction of the Z axis. The vent 104 of this example is made of a material that allows light to pass through. The vent 104 may be an opening.

The light source 2 is fixed on the body 101 such that the generated laser light enters the irradiation controller 108 through the vent 104 and the second space 109. In this example, the light source 2 is located on the negative side of the Z axis with respect to the vent 104.

The body 101 has a shape such that the resonance frequency of the Helmholtz resonance in the first inner space 102 matches with the resonance frequency of the first electrode 12. Alternatively, the shape of the first inner space 102 may be different from that of the above example. The body 101 is an example of the Helmholtz resonator.

The irradiation controller 108 is supported by the body 101. The irradiation controller 108 is located at a position deviated from a straight line extending along the pipe 102*b* in the second space 109. In this example, the irradiation controller 108 is located on the negative side of the Z axis with respect to the pipe 102*b* when being seen along the direction of the Z axis. Alternatively, the irradiation controller 108 may be located on the positive side of the Z axis with respect to the pipe 102*b* when being seen along the direction of the Z axis.

The irradiation controller 108 controls a position irradiated with the laser light generated by the light source 2 to each of multiple positions being different from one another. In this example, the irradiation controller 108 includes a mirror (e.g., a micromirror or a galvano mirror) having a reflecting face that reflects the laser light entered through the vent 104 thereon, and changes the direction of the reflecting face to change the position to be irradiated with the laser light. The change of the position irradiated with light may be referred to as scanning of the laser light. Alternatively, the irradiation controller 108 may be equipped with a mechanism (e.g., a deformable mirror) that changes the focus, and may change the position irradiated with the laser light using the mechanism.

As described above, the detecting device 100C of the second modification to the second embodiment ensures the same effects and advantages as those of the detecting device 100A of the second embodiment.

Furthermore, in the detecting device 100C of the second modification to the second embodiment, the irradiation controller 108 controls a position irradiated with the generated laser light to each of multiple positions being different from one another.

This allows the detecting device 100C to detect a target at respective different positions. For example, a spatial distribution of the target can be obtained.

In addition, the irradiation controller 108 of the detecting device 100C of the second modification to the second embodiment is located at a position deviated from a straight line extending along the pipe 102*b*.

This can reduce the extent of hindering the elastic wave from propagating to the opening 103 by the irradiation controller 108.

Third Modification to Second Embodiment

Here, description will now be made in relation to a detecting device according to a third modification to the second embodiment. The detecting device of the third modification to the second embodiment is different from the detecting device to the second modification to the second embodiment in the point of vibrating the wall that forms a space to be used for Helmholtz resonance. Hereinafter, description will focus on the difference of the detecting device of the third modification to the second modification from that of the second modification to the second embodiment. Like reference numbers designate the same or similar parts and elements between the second modification and the third modification to the second embodiment.

Figure 15:
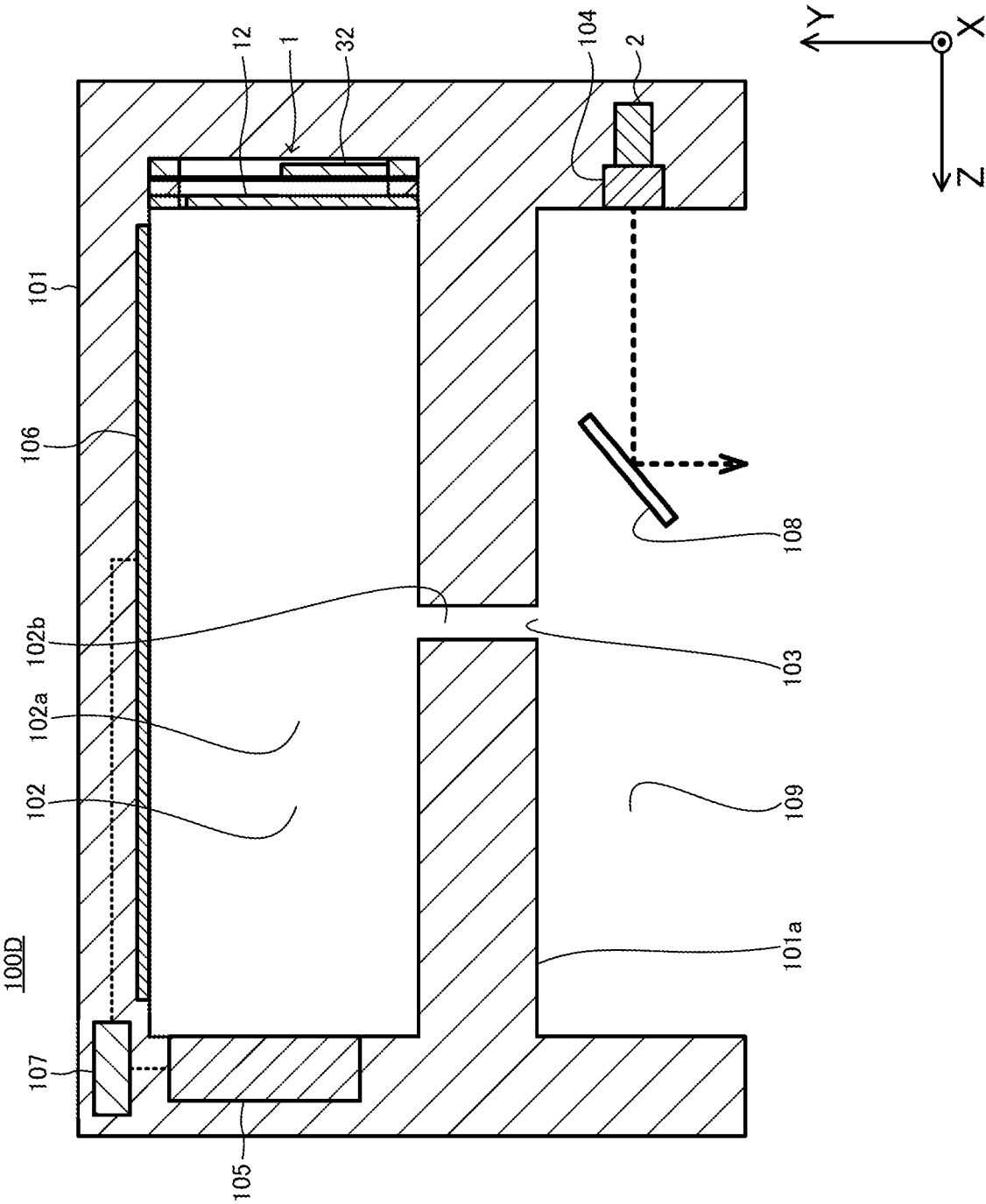
FIG. 15 is a sectional view of a detecting device according to a third modification to the second embodiment.

As illustrated in FIG. 15, a detecting device 100D of the third modification to the second embodiment includes a detector 105, a diaphragm 106, and a vibration controller 107 in addition to the elements in the detecting device 100C of the second modification to the second embodiment.

The detector 105 is a sensor that detects an elastic wave propagating through the air. In this example, the detector 105 has a frequency band of a detectable elastic wave wider than that for the detector 1. Furthermore, the detector 105 has a quicker response of detecting an elastic wave than the detector 1. An example of the detector 105 is a capacitive sensor having a diaphragm structure.

The detector 105 is embedded in a wall forming the base 102a of the body 101 so as to be in contact with the base 102a. Consequently, the detector 105 is fixed on the body 101. In this example, the detector 105 is located on the wall forming the end face on the positive side of the Z axis of the base 102a.

The diaphragm 106 is vibratably embedded in the wall forming the base 102a of the body 101 so as to be in contact with the base 102a. In this example, the diaphragm 106 is located on the wall forming the end face on the positive side of the Y axis of the base 102a. The diaphragm 106 includes an actuator, which causes the diaphragm 106 to vibrate. The actuator of this example is a piezoelectric actuator, but may alternatively be of another type (such as an electromagnetic actuator).

The vibration controller 107 controls the vibration of the diaphragm 106 on the basis of a result of the detection by the detector 105. The vibration controller 107 of this example removes noise from a signal detected by the detector 105 with a filter (e.g., a low-pass filter), adjusts the amplitude and the phase of a signal subjected to the removal, and outputs the adjusted signal as a driving signal to the actuator.

The control of the vibration of the diaphragm 106 by the vibration controller 107 may be referred to as feedback control. Specifically, the vibration controller 107 of this example adjusts the amplitude in order to suppress oscillation caused by the feedback control. For example, the total of the gain in the feedback control may be set to be one or less. In addition, the vibration controller 107 adjusts the phase of the driving signal to lag 90 degrees behind the phase of the signal detected by the detector 105.

The above feedback control amplifies the resonance of the air in the first inner space 102 of the body 101. In this example, the feedback control can be regarded as electromechanical active control on the Q value of a Helmholtz resonator.

As described above, the detecting device 100D of the third modification to the second embodiment brings the same effects and advantages as those of the detecting device 100C of the second modification to the second embodiment.

Furthermore, in the detecting device 100D of the third modification of the second embodiment, the body 101 includes the diaphragm 106 vibratably provided on the wall forming the first inner space 102. The detecting device 100D further includes the second detector 105 that has a frequency band of a detectable elastic wave wider than that for the detector 1 serving as a first detector, that detects an elastic wave propagating through air, and that is in contact with the first inner space 102. In addition, the detecting device 100D further includes the vibration controller 107 that controls the vibration of the diaphragm 106 on the basis of the result of the detecting by the second detector 105.

This configuration can amplify resonance of the air in the first inner space 102 of the body 101. Consequently, an elastic wave having a particular frequency can be detected more precisely.

Alternatively, the detecting device 100D may omit the detector 105 and control the vibration of the diaphragm 106 on the basis of the result of the detection by the detector 1.

Third Embodiment

Here, description will now be made in relation to a detecting device according to a third embodiment. The detecting device of the third embodiment is different from the detecting device of the first embodiment in the point of estimating the position of the wave source of an elastic wave using multiple detectors. Hereinafter, description will focus on the difference of the detecting device of the third embodiment from that of the first embodiment. Like reference numbers designate the same or similar parts and elements between the first embodiment and the third embodiment.

Figure 16:
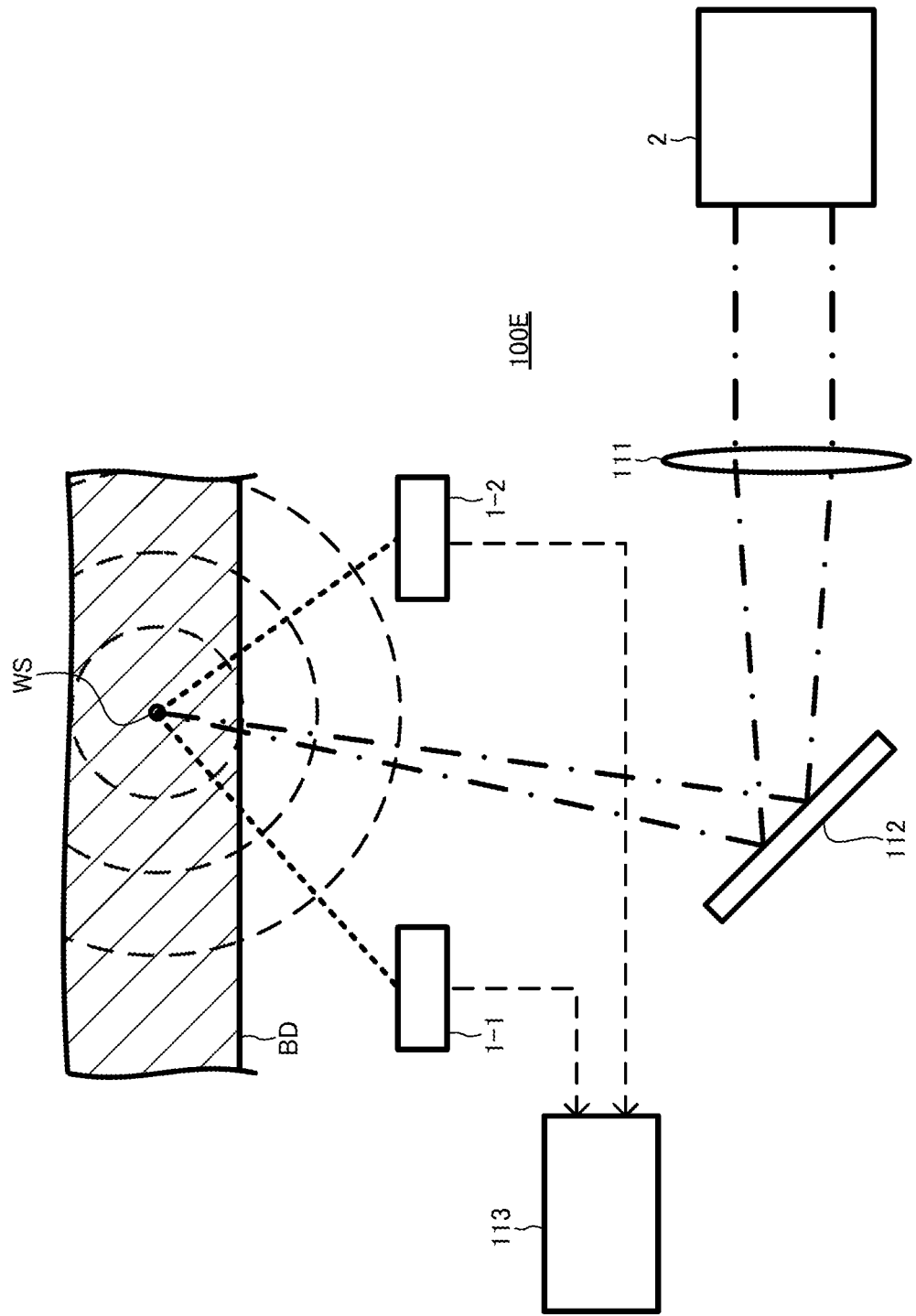
FIG. 16 is a block diagram illustrating an example of the configuration of a detecting device according to a third embodiment.

As illustrated in FIG. 16, the detecting device 100E according to the third embodiment includes two detectors 1-1, 1-2, a light source 2, a lens 111, an irradiation controller 112, and a processor 113.

Each of the detectors 1-1, 1-2 has the same configuration as the detector 1 of the first embodiment. The lens 111 causes the laser light that enters the lens 111 from the light source 2 to form an image on a predetermined position in a living body BD.

The irradiation controller 112 controls a position irradiated with the laser light generated by the light source 2 to each of multiple positions being different from one another. In this example, the irradiation controller 112 includes a mirror (e.g., a micromirror or a galvano mirror) having a reflecting face that reflects the laser light entered through the lens 111 thereon, and changes the direction of the reflecting face to change the position to be irradiated with the light. The change of the position irradiated with light may be referred to as scanning of the laser light. Alternatively, the irradiation controller 112 may be equipped with a mechanism (e.g., a deformable mirror) that changes the focus, and may change the position irradiated with the laser light using the mechanism.

The processor 113 obtains a time period from a time point at which the laser light is generated by the light source 2 to a time point at which an elastic wave is detected by each of the detectors 1-1, 1-2. The processor 113 estimates the position WS of the wave source of the elastic wave on the basis of the obtained time periods.

For example, the processor 113 obtains a time period t1 from the generation of the laser light by the light source 2 to the detection of an elastic wave by the detector 1-1, and obtains a time period t2 from the generation of the laser light by the light source 2 to the detection of the elastic wave by the detector 1-2.

The processor 113 estimates the distance R1 between the detector 1-1 and the position WS of the wave source of the elastic wave by multiplying the time period t1 and the velocity v of the elastic wave. For example, the processor 113 retains the velocity v of the elastic wave in advance. Alternatively, the processor 113 may detect the temperature and estimate the velocity v of the elastic wave based on the detected temperature. Likewise, the processor 113 estimates the distance R2 between the detector 1-2 and the position WS of the wave source of the elastic wave by multiplying the time period t2 and the velocity v of the elastic wave.

Figure 17:
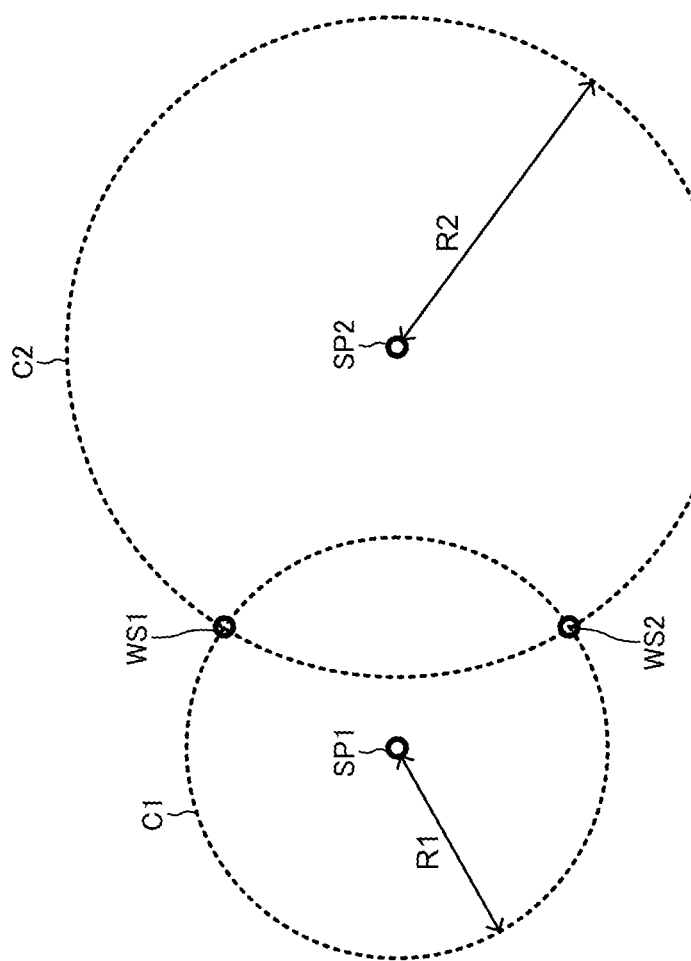
FIG. 17 is a diagram illustrating estimation of the position of a wave source by a processor of FIG. 16.

As illustrated in FIG. 17, the processor 113 further calculates the positions WS1 and WS2 of the crossings of a circle C1 and a circle C2. The circle C1 has the center at the position SP1 of the detector 1-1 and a radius R1. The circle C2 has the center at the position SP2 of the detector 1-2 and a radius R2. Then the processor 113 estimates one of the calculated positions WS1 and WS2 to be the position WS of the wave source of the elastic wave.

As described above, the detecting device 100E of the third embodiment ensures the same effects and advantages as those of the detecting device 100 of the first embodiment.

Furthermore, in the detecting device 100E of the third embodiment, the irradiation controller 112 controls a position irradiated with the generated laser light to each of multiple positions being different from one another.

This allows the detecting device 100E to detect a target at respective different positions. For example, the spatial distribution of the target can be obtained.

Besides, in the detecting device 100E of the third embodiment, the processor 113 estimates the position WS of the wave source of the elastic wave on the basis of the respective time periods from the generation of the laser light to the detection of an elastic wave by the detectors 1-1, 1-2.

This allows the detecting device 100E to precisely estimate the position WS of the wave source of the elastic wave, so that the position of the target that generates the elastic wave can be precisely estimated. For example, a spatial distribution of a target can be precisely obtained.

Alternatively, the detecting device 100E may include three or more detectors. For example, assuming that the detecting device 100E includes three detectors, the processor 113 obtains the time periods t1-t3 from the generation of the laser light by the light source 2 to the detection of an elastic wave by the respective three detectors. Then the processor 113 estimates the respective distances R1-R3 between the three detectors and the position WS of the wave source of the elastic wave by multiplying the respective time periods t1-t3 and the velocity v of the elastic wave.

Figure 18:
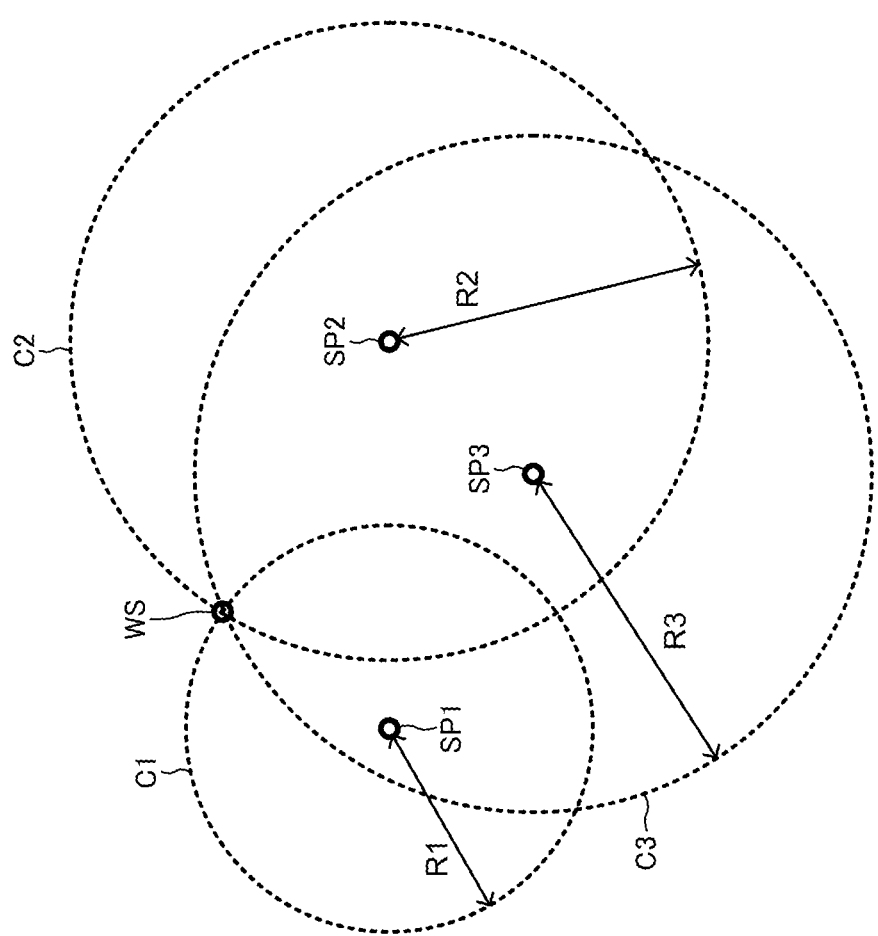
FIG. 18 is a diagram illustrating estimation of the position of a wave source by a processor according to a modification to the third embodiment.

As illustrated in FIG. 18, the processor 113 calculates the position WS of the crossing of a circle C1, a circle C2, and a circle C3. The circle C1 has the center at the position SP1 of the detector 1-1 and a radius R1. The circle C2 has the center at the position SP2 of the detector 1-2 and a radius R2. The circle C3 has the center at the position SP3 of the detector 1-3 and a radius R3. The processor 113 estimates the calculated position WS to be the position WS of the wave source of the elastic wave.

This can further precisely estimate the position WS of the wave source of the elastic wave.

The detecting device 100E may include, in place of each of the detectors 1-1, 1-2, a diaphragm having a cantilever structure and a piezoelectric element that detects deformation of the diaphragm, and may further include a detector that detects an elastic wave on the basis of deformation of the diaphragm. Alternatively, the detecting device 100E may include, in place of each of the detectors 1-1, 1-2, a diaphragm having a cantilever structure, a light source generating a laser light to irradiate the diaphragm, and multiple light detectors that detect a change in direction of the laser light reflected from the diaphragm by detecting the laser light reflected from the diaphragm at each of multiple positions, and may also include a detector that detects an elastic wave on the basis of the change in direction of the laser light reflected from the diaphragm.

The detecting device 100E may include a body having an inner space to resonate air by an elastic wave likewise the detecting device 100A of the second embodiment. In this case, the multiple detectors 1-2, 1-2 are provided to the body. Further alternatively, the detecting device 100E may include a body having an inner space to resonate air by an elastic wave for each detector.

The present invention should by no means be limited to the foregoing embodiments. For example, various modifications and changes that those ordinary skilled in the art understand can be added to the above embodiments without departing from the spirit of the present invention. For example, a combination of the above embodiments and modifications can be adopted as an additional modification to the embodiments within the scope of the present invention.

What is claimed is:

1. A detecting device, comprising:
a light source configured to irradiate a target with light; and
a detector configured to detect a photoacoustic elastic wave propagating through air, the photo-acoustic elastic wave being generated by the target irradiated with light from the light source;
the detector comprising:
a first electrode that is a plate including a cantilever structure with a fixed end and a free end and that is configured to vibrate by being bent by the photoacoustic elastic wave; and
a second electrode that is a plate, that is opposed to the first electrode, and that has a predetermined distance from the first electrode, wherein
the detector is configured to detect the photoacoustic elastic wave on a basis of a change in capacitance between the first electrode and the second electrode,
an end of the second electrode in a direction from the fixed end to the free end is closer to the fixed end than the free end.

2. The detecting device according to claim 1, further comprising:
a first electrode layer;
an insulation layer that includes insulator material and that is in contact with the first electrode layer; and
a second electrode layer that is in contact with the insulation layer on the opposite side of the first electrode layer, wherein
the first electrode layer comprises the first electrode and a first support configured to support the first electrode,
the second electrode layer comprises the second electrode and a second support configured to support the second electrode,
the fixed end of the first electrode is coupled to the first support,
a portion of an end of the first electrode except for the fixed end is spaced apart from the first support,
the insulation layer includes a first penetrating hole configured to open at a portion opposed to the first electrode, and
the second electrode layer includes a second penetrating hole configured to open at a portion that is opposed to the first electrode and that is closer to the free end than the second electrode in the direction from the fixed end to the free end.

3. The detecting device according to claim 1, wherein the second electrode comprises a plurality of penetrating holes.

4. The detecting device according to claim 1, wherein the light is either of a pulsed light or a laser light.

5. The detecting device according to claim 1, wherein oscillation cycle of a pulsed light or a laser light is set to correspond to a resonance frequency of the first electrode.

6. The detecting device according to claim 1, comprising:
a body that includes an inner space being in contact with the detector and an opening being communicated with the inner space.

7. The detecting device according to claim 6, wherein the body has a vent through which the light generated by the light source passes.

8. The detecting device according to claim 7, wherein the vent is located at the same side as the detector with respect to the inner space.

9. The detecting device according to claim 7, wherein the inner space includes a base and a pipe configured to communicate the base with the opening; and
at least part of the pipe extends along a straight line connecting the vent to the opening.

10. The detecting device according to claim 7, wherein further comprising an irradiation controller configured to control a position irradiated with the generated light to each of a plurality of positions being different from one another.

11. The detecting device according to claim 6, wherein the body includes a diaphragm that is vibratably provided on a wall of the inner space, and
the detecting device further comprises:
a second detector that has a frequency band of a detectable photoacoustic elastic wave wider than that for the detector serving as a first detector, configured to detect an photoacoustic elastic wave propagating through air, and that is in contact with the inner space; and
a vibration controller configured to control vibration of the diaphragm on the basis of a result of the detecting by the second detector.

12. The detecting device according to claim 6, wherein the body includes a shape such that a resonance frequency of Helmholtz resonance in the inner space matches with a resonance frequency of the first electrode.

13. The detecting device according to claim 6, wherein the light source is configured to generate light beams comprising respective different wavelengths, and
wherein the detecting device is configured to detect a plurality of photoacoustic elastic waves respectively generated by irradiations with the light beams and detects an photoacoustic elastic wave generated by the target on the basis of a result of the detecting.

14. A detecting device, comprising:
a light source configured to irradiate a target with light;
a plurality of detectors configured to detect a photoacoustic elastic wave propagating through air, the photoacoustic elastic wave being generated by the target irradiated with light from the light source;
the detectors each comprising:
a first electrode that is a plate including a cantilever structure with a fixed end and a free end and that vibrates by being bent by the photoacoustic elastic wave; and
a second electrode that is a plate, that is opposed to the first electrode, and that has a predetermined distance from the first electrode, wherein
each detector is configured to detect the photoacoustic elastic wave on a basis of a change in capacitance between the first electrode and the second electrode, an end of the second electrode in a direction from the fixed end to the free end being closer to the fixed end than the free end; and
processor circuitry configured to estimate a position of a wave source of the photoacoustic elastic wave on the basis of a time period from a time point at which the light is generated to a time point at which each of the plurality of detectors is configured to detect the elastic wave.

15. The detecting device according to claim 14, further comprising an irradiation controller configured to control a position irradiated with the generated light to each of a plurality of positions being different from one another.

16. The detecting device according to claim 14, wherein the light source is configured to generate light beams having respective different wavelengths, and
wherein the detecting device is configured to detect a plurality of photoacoustic elastic waves respectively generated by irradiations with the light beams and is configured to detect an photoacoustic elastic wave generated by the target on the basis of a result of the detecting.

* * * * *